(12) United States Patent
Kim et al.

(10) Patent No.: US 8,808,880 B2
(45) Date of Patent: Aug. 19, 2014

(54) CONDENSED-CYCLIC COMPOUND, ORGANIC LIGHT-EMITTING DEVICE COMPRISING THE SAME, AND FLAT PANEL DISPLAY APPARATUS

(75) Inventors: Hee-Yeon Kim, Yongin (KR); Seung-Gak Yang, Yongin (KR); Jeoung-In Yi, Yongin (KR); Jae-Yong Lee, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 503 days.

(21) Appl. No.: 13/243,959

(22) Filed: Sep. 23, 2011

(65) Prior Publication Data
US 2012/0286247 A1 Nov. 15, 2012

(30) Foreign Application Priority Data

May 11, 2011 (KR) ........................ 10-2011-0044076

(51) Int. Cl.
*H01L 51/54* (2006.01)
*C07D 209/56* (2006.01)

(52) U.S. Cl.
USPC ........... 428/690; 428/917; 313/504; 313/506; 548/420; 257/40

(58) Field of Classification Search
None
See application file for complete search history.

(56) References Cited

U.S. PATENT DOCUMENTS

| 2004/0106514 A1* | 6/2004 | Nagy et al. ................ 502/155 |
| 2007/0231503 A1 | 10/2007 | Hwang et al. |
| 2008/0107919 A1 | 5/2008 | Hwang et al. |
| 2008/0160347 A1 | 7/2008 | Wang et al. |

FOREIGN PATENT DOCUMENTS

| JP | 2008285561 | 11/2008 |
| KR | 10-2005-0097670 A | 10/2005 |
| KR | 10-2006-0005755 A | 1/2006 |
| KR | 10-2007-0114562 A | 12/2007 |
| KR | 2007-0114669 A | 12/2007 |
| KR | 1020080031808 | 4/2008 |
| WO | WO 2010/110553 | * 9/2010 |

\* cited by examiner

*Primary Examiner* — Dawn Garrett
(74) *Attorney, Agent, or Firm* — Robert E. Bushnell, Esq.

(57) ABSTRACT

A condensed-cyclic compound represented by Formula 1 below, an organic light-emitting device including the same, and a flat panel display apparatus including the organic light-emitting device:

<Formula 1>

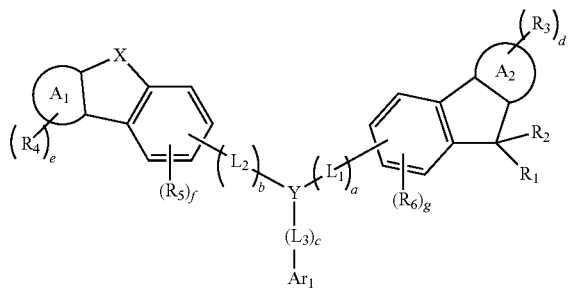

wherein, X, Y, $A_1$, $A_2$, $L_1$, $L_2$, $L_3$, $Ar_1$, $R_1$, $R_2$, $R_3$, $R_4$, $R_5$, $R_6$, a, b, c, d, e, f, and g are described in the detailed description of the invention. The organic light-emitting device including an organic layer including the compound above has low driving voltage, high emission efficiency, and long lifetime.

20 Claims, 2 Drawing Sheets

FIG. 2

A first electrode 12 may be formed by providing a first electrode material on the substrate 11 using deposition or sputtering

A hole injection layer 13 is formed on the first electrode 12

A hole transport layer 14 is formed on the hole injection layer 13 by using vacuum deposition, a wet process, and laser transferring

An emission layer 15 may be formed on the hole transport layer 14

When a phosphorescent dopant is included in the emission layer 15, a hole blocking layer may be formed between the emission layer 15 and the hole transport layer 16

An electron transport layer 16 is formed by using vacuum deposition, a wet process, or laser transferring

An electron injection layer 17, which facilitates electron injection from a cathode, may be formed on the electron transport layer 16

The second electrode 18 may be formed on the electron injection layer 17

CONDENSED-CYCLIC COMPOUND, ORGANIC LIGHT-EMITTING DEVICE COMPRISING THE SAME, AND FLAT PANEL DISPLAY APPARATUS

CLAIM OF PRIORITY

This application claims the benefit of Korean Patent Application No. 10-2011-0044076, filed on May 11, 2011, in the Korean Intellectual Property Office, the disclosure of which is incorporated herein in its entirety by reference.

BACKGROUND OF THE INVENTION

1. Field of the Invention

The present invention relates to a condensed-cyclic compound, an organic light-emitting device including the same, and a flat panel display apparatus including the organic light-emitting device, and more particularly, to a condensed-cyclic compound which is suitable to be used in a hole transport layer of an organic light-emitting device, the organic light-emitting device including the condensed-cyclic compound, and a flat panel display apparatus including the organic light-emitting device. The organic light-emitting device that includes an organic layer including the condensed-cyclic compound has characteristics of low driving voltage, high light-emitting efficiency, and long lifetime.

2. Description of the Related Art

Organic light-emitting devices are self light-emitting devices which have wide viewing angles, excellent contrast, rapid response times, excellent brightness, driving voltage, and response speeds, and are multicolored.

In a general organic light-emitting device, an anode is formed on a substrate, and a hole transport layer, an emission layer, an electron transport layer, and a cathode are sequentially formed on the anode. Here, the hole transport layer, the emission layer, and the electron transport layer are organic thin film layers including an organic compound.

A driving principle of the organic light-emitting device is as follows. When voltage is applied between the anode and the cathode, holes injected from the anode move to the emission layer through the hole transport layer, and electrons injected from the cathode move to the emission layer through the electron transport layer. Carriers such as the holes and the electrons are recombined at the emission layer and produce excitons. Such excitons are changed from an excitation state to a ground state, thereby generating light.

A general organic light-emitting device still needs to be improved in terms of driving voltage, light-emitting efficiency, and lifetime.

SUMMARY OF THE INVENTION

The present invention provides a condensed-cyclic compound, an organic light-emitting device including the condensed-cyclic compound, and a flat panel display apparatus including the organic light-emitting device.

According to an aspect of the present invention, there is provided a condensed-cyclic compound represented by Formula 1 below:

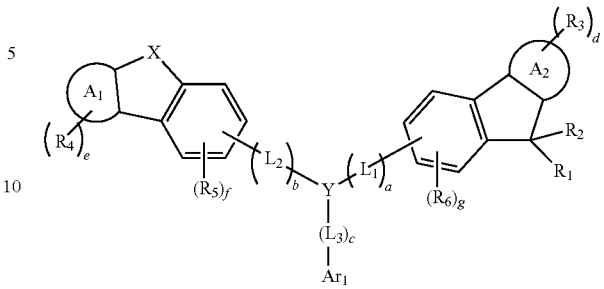

<Formula 1> wherein X is $N(Ar_2)$ or S;
Y is N, B, or P;
$A_1$ and $A_2$ are bicyclic aromatic rings;
$L_1$, $L_2$ and $L_3$ are each independently one selected from the group consisting of a substituted or unsubstituted $C_1$-$C_{30}$ alkylene group, a substituted or unsubstituted $C_5$-$C_{30}$ arylene group, and a substituted or unsubstituted divalent $C_2$-$C_{30}$ heterocyclic group;
$Ar_1$ and $Ar_2$ are each independently one selected from the group consisting of a hydrogen atom, deuterium, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, a substituted or unsubstituted $C_2$-$C_{30}$ heterocyclic group, a group represented by $N(Q_1)(Q_2)$, and a group represented by $Si(Q_3)(Q_4)(Q_5)$, $Q_1$ through $Q_5$ are each independently one selected from the group consisting of a hydrogen atom, deuterium, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, and a substituted or unsubstituted $C_2$-$C_{30}$ heterocyclic group;
$R_1$, $R_2$, $R_3$, $R_4$, $R_5$, and $R_6$ are each independently one selected from the group consisting of a hydrogen atom, deuterium, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_1$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, and a substituted or unsubstituted $C_2$-$C_{30}$ heterocyclic group, wherein at least two of $R_3$ through $R_6$ that are adjacent to each other may be combined with each other to form a saturated or unsaturated ring and plural groups in $R_3$ through $R_6$ may be the same as each other or different from each other; and a, b, and c are each independently one of fixed numbers from 0 to 5, d and e are each independently one of fixed numbers from 1 to 10, and f and g are each independently one of fixed numbers from 1 to 3.

According to another aspect of the present invention, there is provided an organic light-emitting device including: a first electrode; a second electrode facing the first electrode; and an organic light-emitting device comprising at least one organic layer interposed between the first electrode and the second electrode, wherein the at least one organic layer comprises the condensed-cyclic compound represented by Formula 1 above.

According to another aspect of the present invention, there is provided a flat panel display apparatus comprising a transistor comprising a source electrode, a drain electrode, a gate, and an active layer, and the organic light-emitting device above, wherein a first electrode of the organic light-emitting device is electrically connected to the source electrode or the drain electrode.

BRIEF DESCRIPTION OF THE DRAWINGS

The above and other features and advantages of the present invention will become more apparent by describing in detail exemplary embodiments thereof with reference to the attached drawings in which:

FIG. 2 is a flow chart showing a method of making an organic light emitting device according to an embodiment of the present invention.

DETAILED DESCRIPTION OF THE INVENTION

Figure 1:
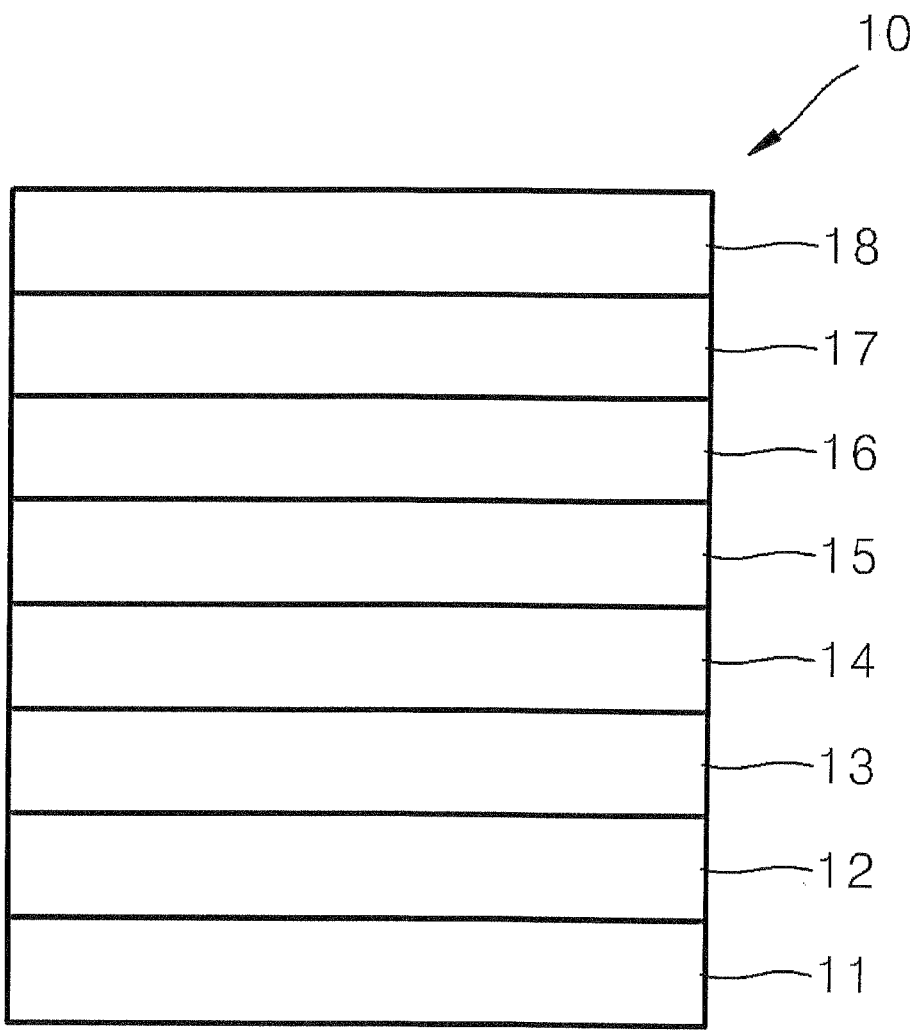
FIG. 1 is a cross-sectional view of an organic light-emitting device according to an embodiment of the present invention.

A condensed-cyclic compound represented by Formula 1 below is provided according to an embodiment of the present invention:

<Formula 1>

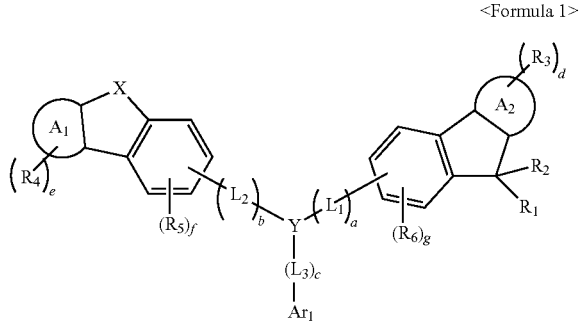

wherein X is $N(Ar_2)$ or S;
Y is N, B, or P;
$A_1$ and $A_2$ are bicyclic aromatic rings;
$L_1$, $L_2$, and $L_3$ are each independently one selected from the group consisting of a substituted or unsubstituted $C_1$-$C_{30}$ alkylene group, a substituted or unsubstituted $C_5$-$C_{30}$ arylene group, and a substituted or unsubstituted divalent $C_2$-$C_{30}$ heterocyclic group;
$Ar_1$ and $Ar_2$ are each independently one selected from the group consisting of a hydrogen atom, deuterium, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, a substituted or unsubstituted $C_2$-$C_{30}$ heterocyclic group, a group represented by $N(Q_1)(Q_2)$, and a group represented by $Si(Q_3)(Q_4)(Q_5)$;

$R_1$, $R_2$, $R_3$, $R_4$, $R_5$, and $R_6$ are each independently one selected from the group consisting of a hydrogen atom, deuterium, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_1$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, and a substituted or unsubstituted $C_2$-$C_{30}$ heterocyclic group, wherein at least two of $R_3$ through $R_6$ that are adjacent to each other may be combined with each other to form a saturated or unsaturated ring and plural groups in $R_3$ through $R_6$ may be the same as each other or different from each other; and a, b, and c are each independently one of the integers from 0 to 5, d and e are each independently one of fixed numbers from 1 to 10, and f and g are each independently one of fixed numbers from 1 to 3.

Here, $Q_1$ through $Q_5$ are each independently one selected from the group consisting of a hydrogen atom, deuterium, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, and a substituted or unsubstituted $C_2$-$C_{30}$ heterocyclic group. For example, $Q_1$ through $Q_5$ may be each independently one selected from the group consisting of a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzoxazolyl group, a substituted or unsubstituted dibenzofuranyl group, and a substituted or unsubstituted dibenzothiophenyl group.

The condensed-cyclic compound represented by Formula 1 above has at least one selected from the group consisting of a structure, in which a bicyclic aromatic ring is fused into indene, and a structure, in which a bicyclic aromatic ring is fused into indoline or benzothiophene. The condensed-cyclic compound has high glass transition temperature and excellent charge transport capability.

For example, the condensed-cyclic compound represented by Formula 1 above may be a compound having at least one benzofluorene structure and at least one benzocarbazole structure, or a compound having at least one benzofluorene structure and at least one benzonaphtothiopene structure.

According to an embodiment of the present invention, X in Formula 1 above may be $N(Ar_2)$. $Ar_2$ is the same as defined above. In this case, the condensed-cyclic compound represented by Formula 1 above may include a structure, in which a bicyclic aromatic ring is fused into indoline, and thus the condensed-cyclic compound may include at least one selected from the group consisting of a structure, in which a bicyclic aromatic ring is fused into indene, and a structure, in which a bicyclic aromatic ring is fused into indoline. In Formula 1 above, the structure, in which a bicyclic aromatic ring is fused into indoline, may be, for example, a carbazole derivative.

According to an embodiment of the present invention, Y in Formula 1 above may be N. In this case, the condensed-cyclic compound represented by Formula 1 above may have a characteristic of an arylamine-based compound.

According to an embodiment of the present invention, $A_1$ and $A_2$ in Formula 1 above may be a $C_8$-$C_{10}$ bicyclic aromatic ring.

In Formula 1 above,

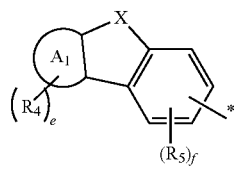

is a structure, in which a bicyclic aromatic ring is fused into indoline or benzothiophene and $A_1$ may be, for example, a fused bicyclic aromatic ring which may contain 8, 9, or 10 carbon atoms.

In Formula 1 above,

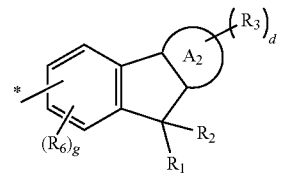

is a structure, in which a bicyclic aromatic ring is fused into indene and $A_2$ may be, for example, a fused bicyclic aromatic ring which may contain 8, 9, or 10 carbon atoms.

According to an embodiment of the present invention, $A_1$ and $A_2$ may be each independently a naphthalene ring containing 10 carbon atoms or an indene ring containing 9 carbon atoms. In this case, in Formula 1 above,

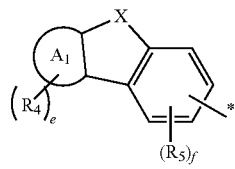

may be a benzocarbazole derivative or a benzonaphtothiopene derivative and

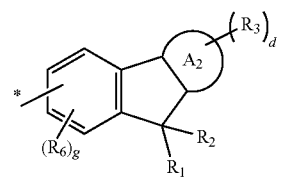

may be a benzofluorene derivative. The condensed-cyclic compound represented by Formula 1 above may have various structures according to locations where the naphthalene ring or the indene ring is fused into indene, indoline, or benzothiophene.

According to an embodiment of the present invention, in Formula 1 above,

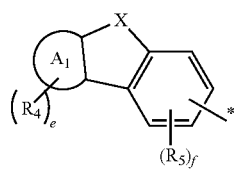

may have a benzocarbazole structure represented by one of Formulas 2A through 2C below:

<Formula 2A>

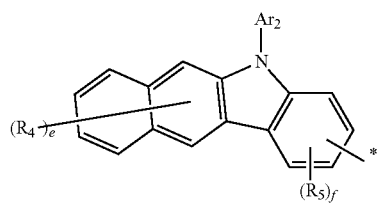

<Formula 2B>

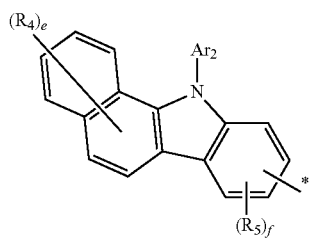

<Formula 2C>

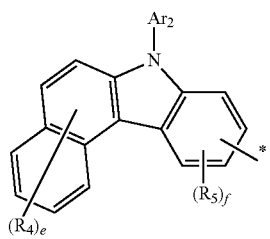

wherein $Ar_2$ is one selected from the group consisting of a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group, $R_4$ and $R_5$ are the same as defined above, e is one of fixed numbers from 1 to 6, and f is one of fixed numbers from 1 to 3.

For example, more specifically, the benzocarbazole structure represented by one of Formulas 2A through 2C may have a benzocarbazole structure represented by one of Formulas 2D through 2O:

<Formula 2D>

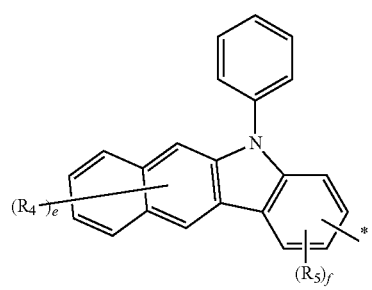

<Formula 2E>

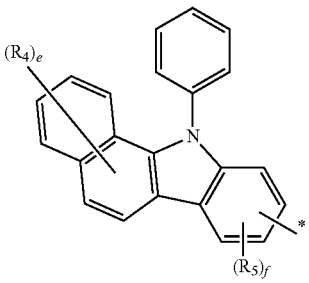

<Formula 2F>

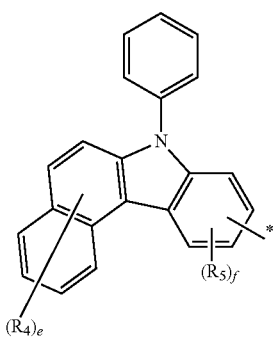

<Formula 2G>

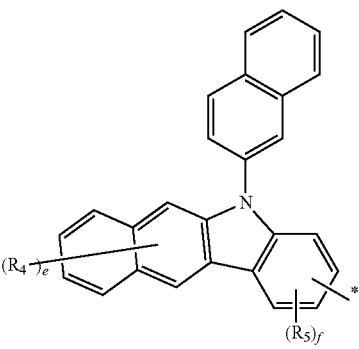

<Formula 2H>

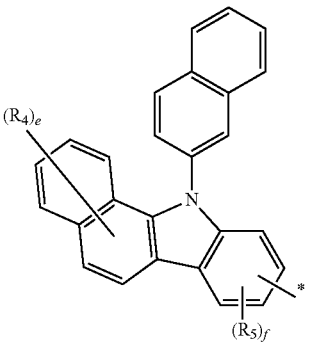

<Formula 2I>
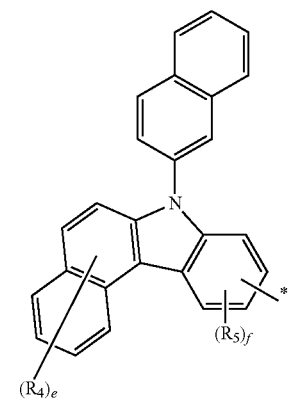

<Formula 2J>
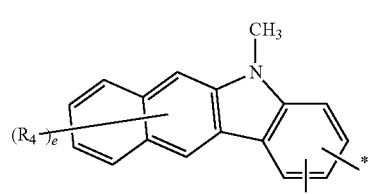

<Formula 2K>
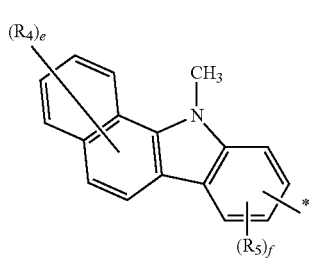

<Formula 2L>
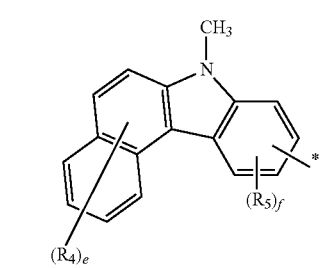

<Formula 2M>
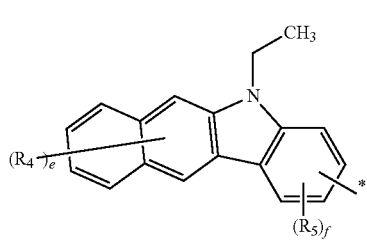

<Formula 2N>
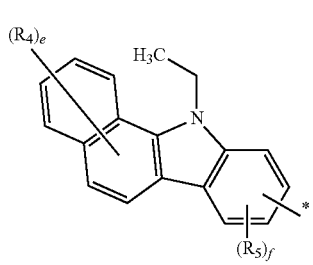

<Formula 2O>
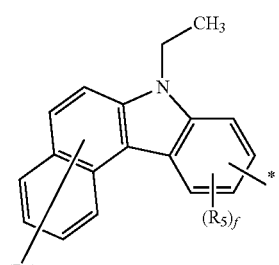

According to an embodiment of the present invention, in Formula 1 above,

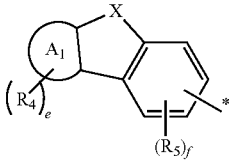

may be a benzonaphtothiopene structure represented by one of Formulas 3A through 3C below:

<Formula 3A>
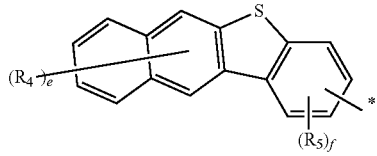

<Formula 3B>
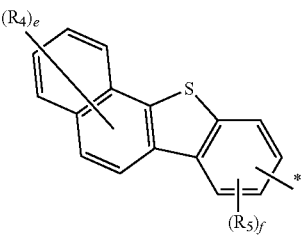

<Formula 3C>
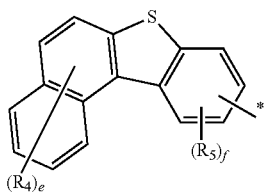

wherein, $R_4$ and $R_5$ are the same as defined in the specification, e is one of fixed numbers from 1 to 6, and f is one of fixed numbers from 1 to 3.

According to an embodiment of the present invention, in Formula 1 above,

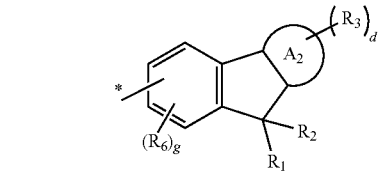

may be a benzofluorene structure represented by one of Formulas 4A through 4C below:

<Formula 4A>

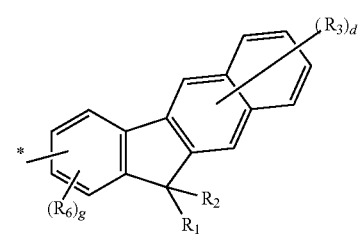

<Formula 4B>

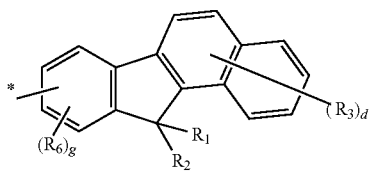

<Formula 4C>

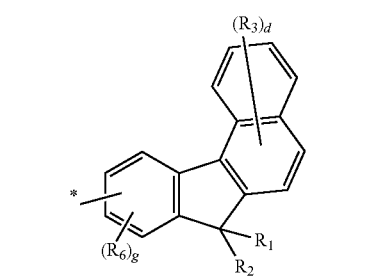

wherein, $R_1$ and $R_2$ are each independently one selected from the group consisting of a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group, $R_3$ and $R_6$ are the same as defined in the specification, d is one of fixed numbers from 1 to 6, and g is one of fixed numbers from 1 to 3.

For example, more specifically, the benzofluorene structure represented by one of Formulas 4A through 4C may have a benzofluorene structure represented by one of Formulas 4D through 4I below:

<Formula 4D>

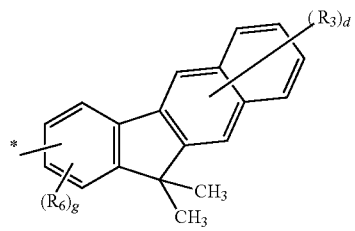

<Formula 4E>

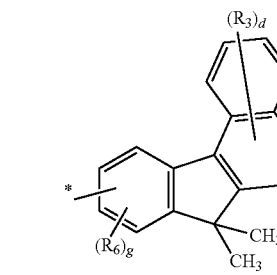

<Formula 4F>

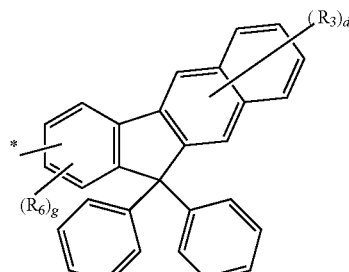

<Formula 4G>

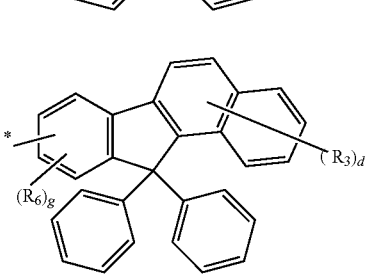

<Formula 4H>

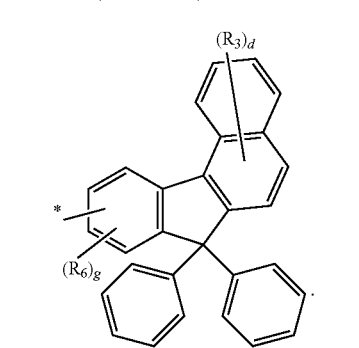

<Formula 4I>

According to an embodiment of the present invention, the condensed-cyclic compound represented by Formula 1 above may be represented by one of Formulas 5A through 5I below:

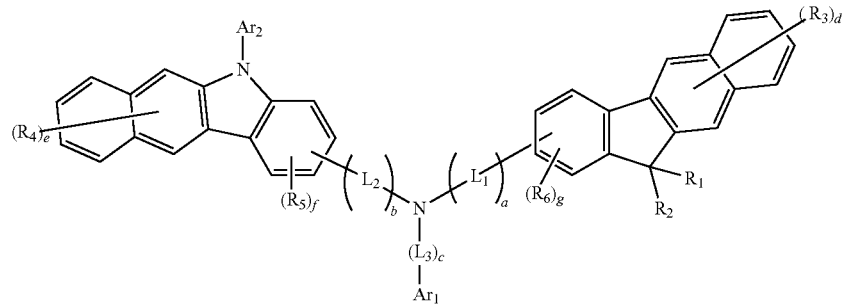
<Formula 5A>
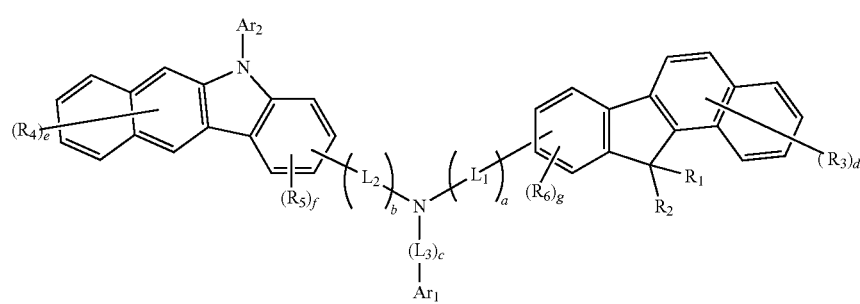
<Formula 5B>
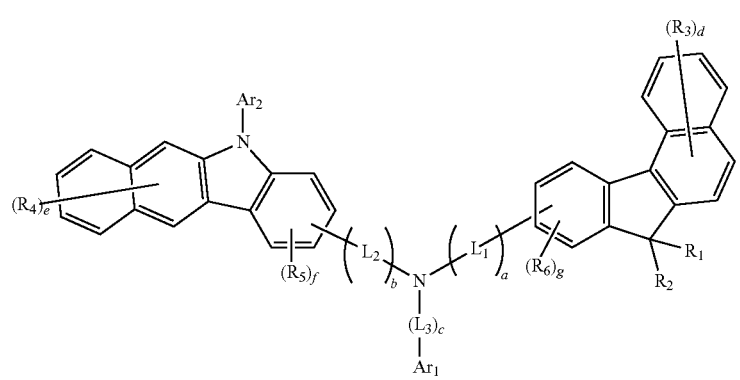
<Formula 5C>
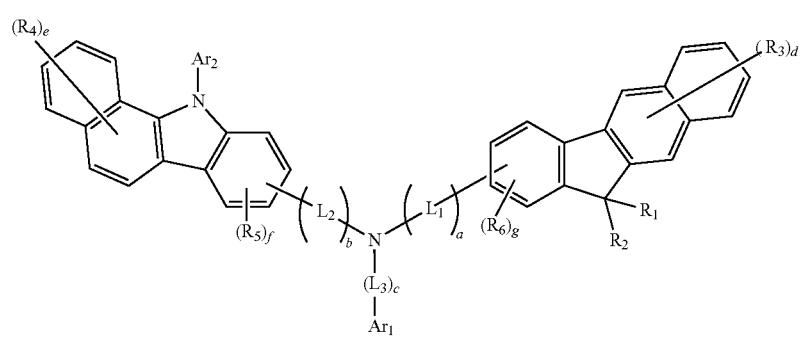
<Formula 5D>
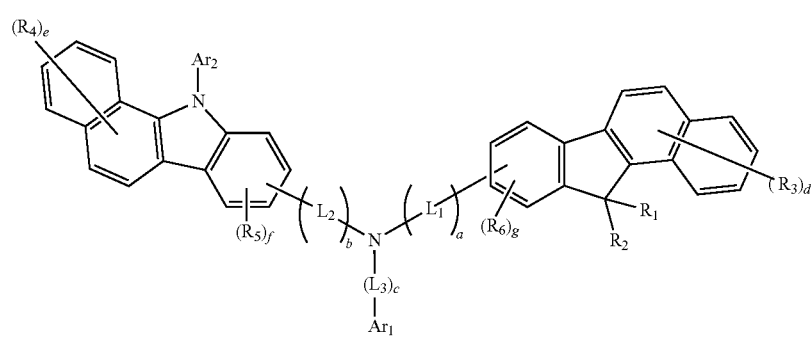
<Formula 5E>

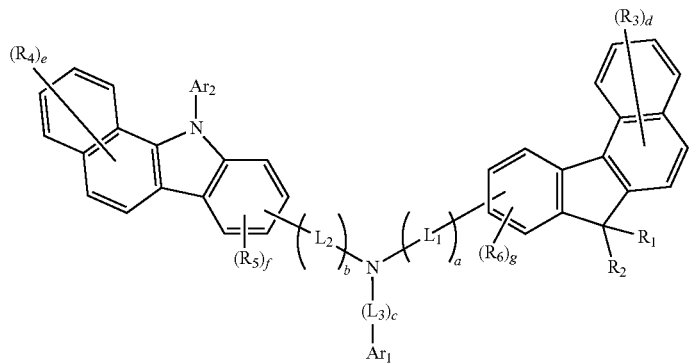

<Formula 5F>

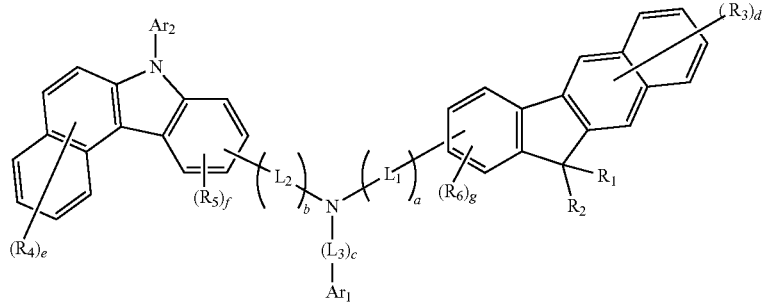

<Formula 5G>

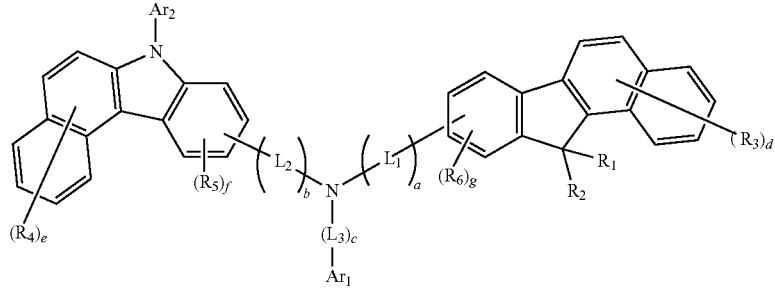

<Formula 5H>

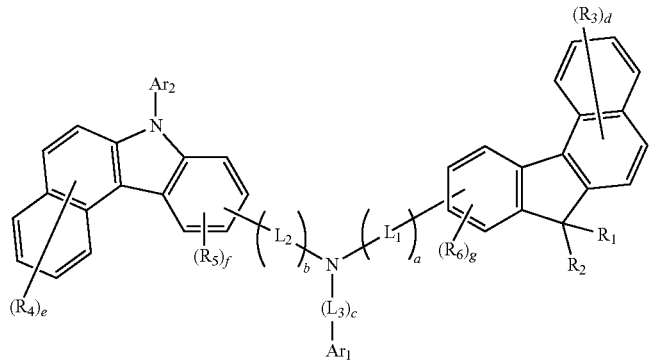

<Formula 5I> wherein, $Ar_1$ and $Ar_2$ are each independently one selected from the group consisting of a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group; $R_1$ and $R_2$ are each independently one selected from the group consisting of a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group; $R_3$, $R_4$, $R_5$, $R_6$, $L_1$, $L_2$, and $L_3$ are the same as defined in the specification; a, b, and c are each independently one of fixed numbers from 0 to 5, d and e are each independently one of fixed numbers from 1 to 6, and f and g are each independently one of fixed numbers from 1 to 3.

According to an embodiment of the present invention, in Formula 1 above, $L_1$, $L_2$, and $L_3$ are each independently one selected from the group consisting of a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, and a substituted or unsubstituted hexylenylene group.

According to an embodiment of the present invention, in Formula 1, a, b, and c may be each independently 0 or 1. When a, b, and c are 0, a single bond is indicated. For example, a, b, and c may be all 0.

According to an embodiment of the present invention, in Formula 1 above, $Ar_1$ and $Ar_2$ may be each independently one selected from the group consisting of a hydrogen atom, deuterium, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenylene group, a substituted or unsubstituted chrysenyl group, a substituted or unsubstituted naphthacenyl group, a substituted or unsubstituted picenyl group, a substituted or unsubstituted perylenylene group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoxazolyl group, a substituted or unsubstituted benzoimidazolyl group, a substituted or unsubstituted furanyl, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzoxazolyl group, a substituted or unsubstituted dibenzofuranyl group, a substituted or unsubstituted dibenzothiophenyl group, a group represented by $N(Q_1)(Q_2)$, and a group represented by $Si(Q_3)(Q_4)(Q_5)$. In particular, $Ar_1$ is disposed at the end in Formula 1 and may be for example, one selected from the group consisting of a substituted or unsubstituted phenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group.

According to an embodiment of the present invention, in Formula 1 above, $R_1$, $R_2$, $R_3$, $R_4$, $R_5$, and $R_6$ may be each independently one selected from the group consisting of a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzoxazolyl group, a substituted or unsubstituted dibenzofuranyl group, and a substituted or unsubstituted dibenzothiophenyl group. For example, $R_1$ and $R_2$ may be each independently one selected from the group consisting of a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group.

For example, Formula 1 above may represent the condensed-cyclic compound, in which $R_3$, $R_4$, $R_5$, and $R_6$ may each be a hydrogen atom and $R_1$ and $R_2$ may each be one selected from the group consisting of a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group.

More specifically, the condensed-cyclic compound represented by Formula 1 above may be, but is not limited to, one of compounds represented by Compounds 1 through 15 below:

<Compound 1>

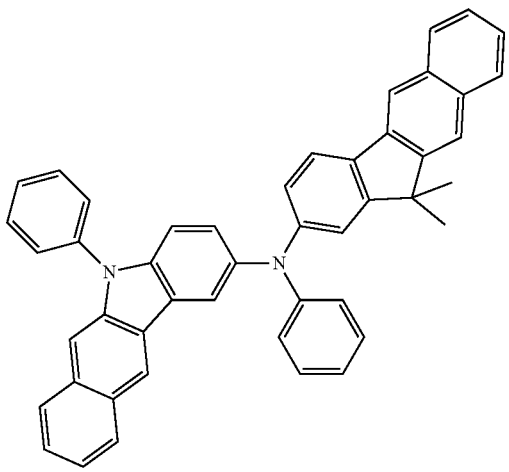

<Compound 2>

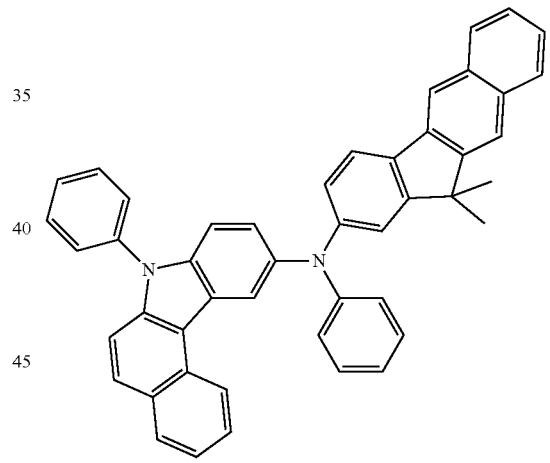

<Compound 3>

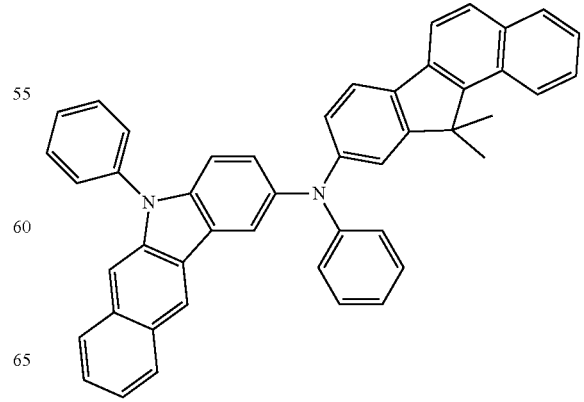

<Compound 4>
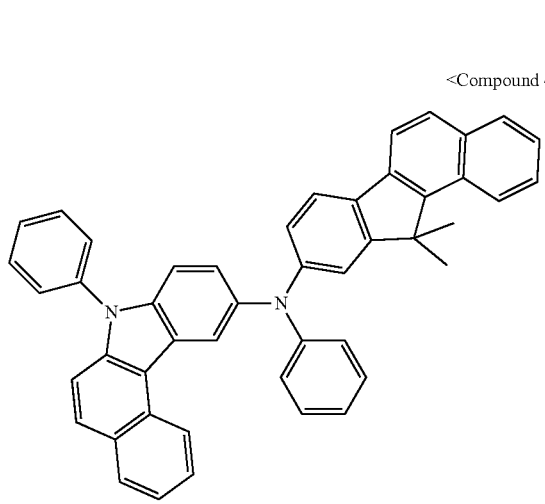
<Compound 5>
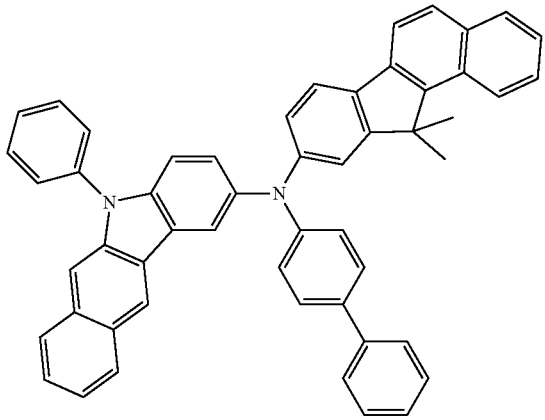
<Compound 6>
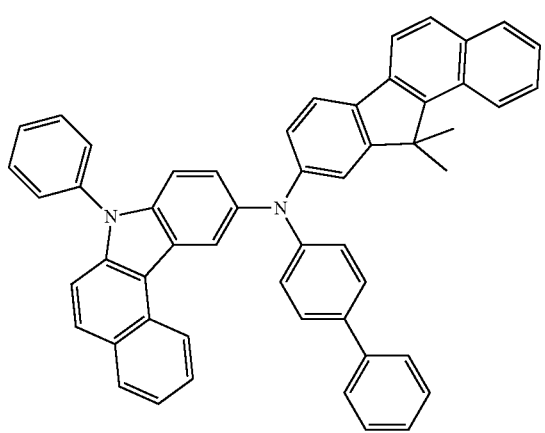
<Compound 7>
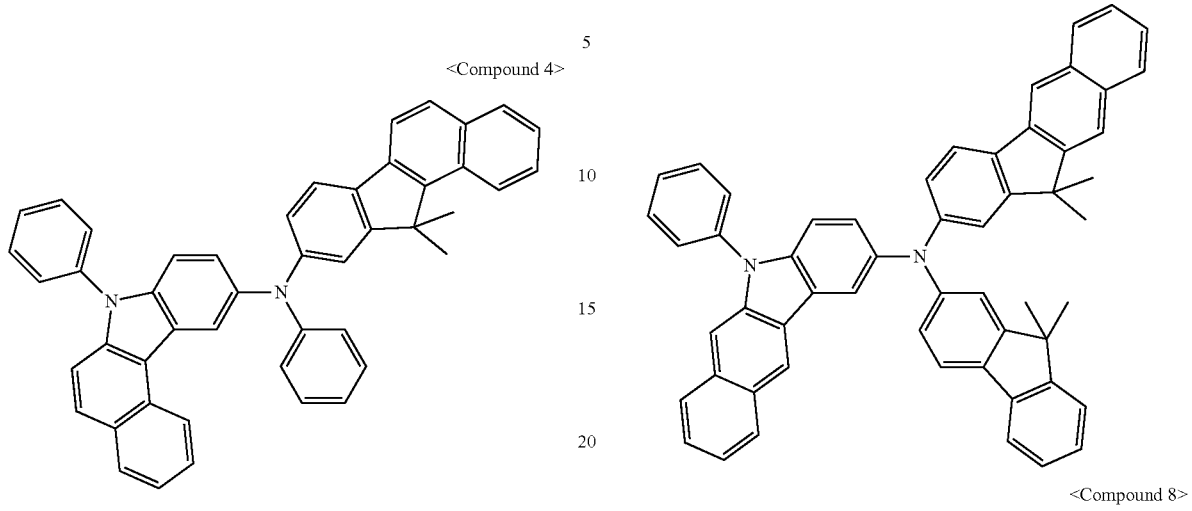
<Compound 8>
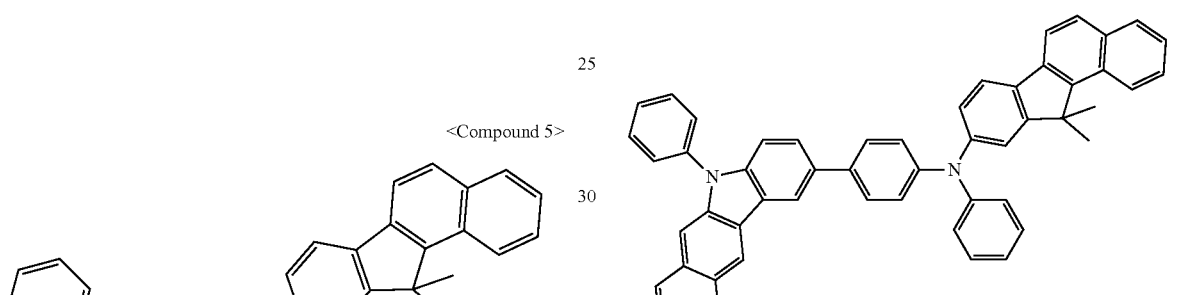
<Compound 9>
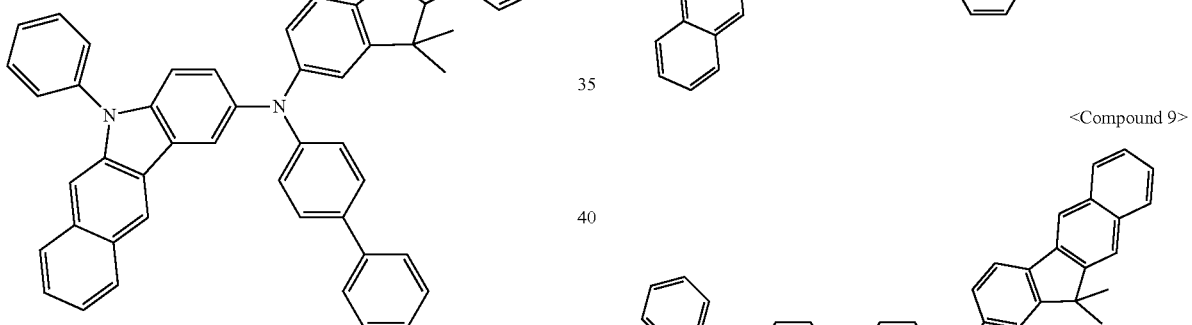
<Compound 10>
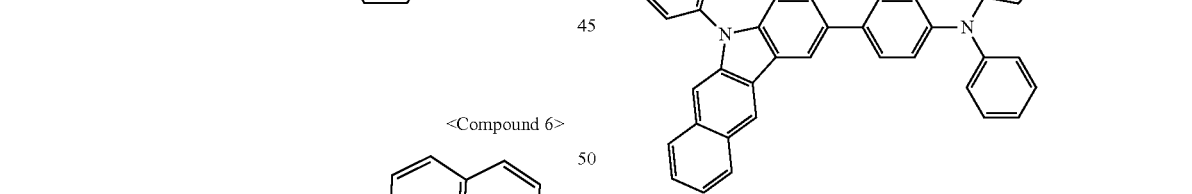

-continued

<Compound 11>
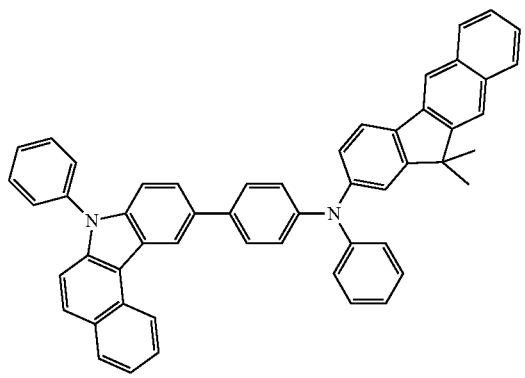

<Compound 15>
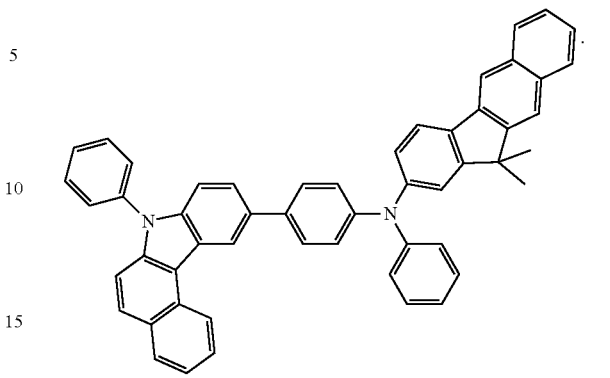

<Compound 12>
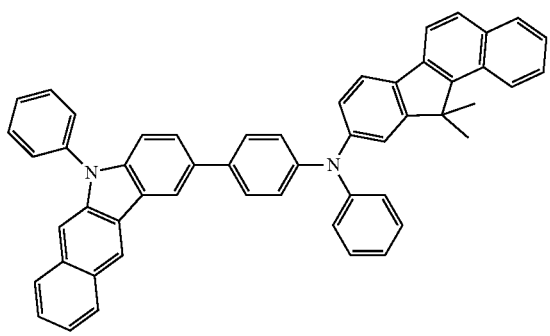

<Compound 13>
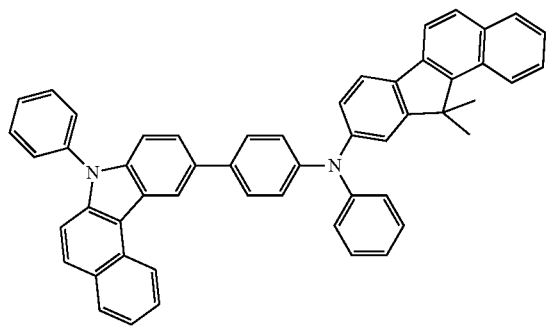

<Compound 14>
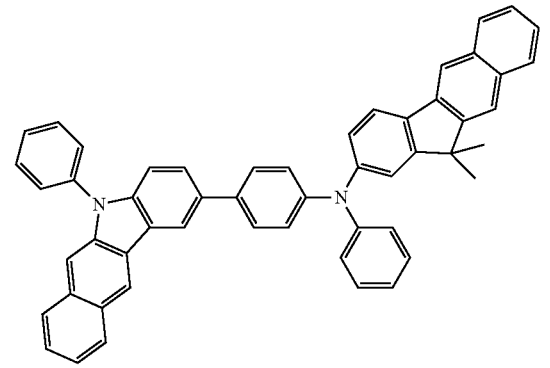

In the expression "substituted or unsubstituted A (A is an arbitrary substituent)," the term "substituted A" denotes "A, in which at least one hydrogen atom of A is substituted with one substituent selected from the group consisting of deuterium, a halogen atom, a hydroxyl group, a cyano group, a nitro group, a carboxyl group or a salt derivative thereof, a sulfonic acid group or a salt derivative thereof, a phosphate group or a salt derivative thereof, a $C_1$-$C_{30}$ alkyl group, a alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_5$-$C_{30}$ aryl group, a $C_5$-$C_{30}$ aryloxy group, a $C_5$-$C_{30}$ arylthio group, a $C_2$-$C_{30}$ heterocyclic group, a group represented by $N(Q_{101})(Q_{102})$, and a group represented by $Si(Q_{103})(Q_{104})(Q_{105})$." Here, $Q_{101}$ through $Q_{105}$ may be each independently a hydrogen atom, deuterium, a halogen atom, a hydroxyl group, a cyano group, an amino group, a nitro group, a carboxyl group, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_5$-$C_{30}$ aryl group, a $C_5$-$C_{30}$ aryloxy group, a $C_5$-$C_{30}$ arylthio group, or a $C_2$-$C_{30}$ heterocyclic group.

For example, "the substituted A" may denote "A, in which at least one hydrogen atom is substituted with deuterium, a halogen atom, a hydroxyl group, a cyano group, a nitro group, a carboxyl group, a methyl group, an ethyl group, a propyl group, a butyl group, a phenyl group, a pentalenyl group, an indenyl group, a naphthyl group, an azulenyl group, a heptalenyl group, an indacenyl group, an acenaphtyl group, a fluorenyl group, a spiro-fluorenyl group, a phenalenyl group, a phenanthrenyl group, an anthryl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl, benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzoxazolyl group, a dibenzofuranyl group, or a dibenzothiophenyl group."

The substituted $C_1$-$C_{30}$ alkyl group denotes a saturated hydrocarbon group having a linear and branched structure in which one hydrogen atom is lacking alkane. Examples of the unsubstituted $C_1$-$C_{30}$ alkyl group may include methyl, ethyl, propyl, isobutyl, sec-butyl, pentyl, iso-amyl, hexyl, and the like. A substituent of the substituted $C_1$-$C_{30}$ alkyl group is described in the description for the "substituted A."

The unsubstituted $C_2$-$C_{30}$ alkenyl group denotes a terminal group containing at least one carbon double bond at the middle or the end of the unsubstituted $C_2$-$C_{30}$ alkyl group. Examples of the unsubstituted $C_2$-$C_{30}$ alkenyl group may include ethenyl, prophenyl, butenyl, pentanyl, hexenyl, heptenyl, octenyl, propadienyl, isoprenyl, allyl, and the like. A substituent of the substituted $C_2$-$C_{30}$ alkenyl group is described in the description for the "substituted A."

The unsubstituted $C_2$-$C_{30}$ alkynyl group denotes a terminal group containing at least one carbon triple bond at the middle or the end of the unsubstituted $C_2$-$C_{60}$ alkyl group. Examples of the unsubstituted $C_2$-$C_{30}$ alkynyl group may include acetylenyl. A substituent of the substituted $C_2$-$C_{30}$ alkynyl group is described in the description for the "substituted A."

The unsubstituted $C_1$-$C_{30}$ alkoxy group has Formula of —OY (Y is the unsubstituted $C_1$-$C_{30}$ alkyl group) and may be, for example, methoxy, ethoxy, isopropyloxy, butoxy, pentoxy, and the like. A substituent of the substituted $C_1$-$C_{30}$ alkoxy group is described in the description for the "substituted A."

The unsubstituted $C_3$-$C_{30}$ cycloalkyl group denotes a ring-type saturated hydrocarbon group and may be, for example, cyclopropyl, cyclobutyl, cyclopentyl, cyclohexyl, cyclooctyl, and the like. A substituent of the substituted $C_3$-$C_{30}$ cycloalkyl group is described in the description for the "substituted A."

The unsubstituted $C_3$-$C_{30}$ cycloalkenyl group denotes a ring-type unsaturated hydrocarbon group which has at least one carbon double bond and is not an aromatic ring. Examples of the unsubstituted $C_3$-$C_{30}$ cycloalkenyl group may include cyclopropenyl, cyclobutenyl, cyclopentenyl, cyclohexenyl, cycloheptenyl, a 1,3-cyclohexadienyl group, a 1,4-cyclohexadienyl group, a 2,4-cycloheptadienyl group, a 1,5-cyclooctadienyl group, and the like. A substituent of the substituted $C_3$-$C_{60}$ cycloalkenyl group is described in the description for the "substituted A."

The unsubstituted $C_5$-$C_{30}$ aryl group denotes a monovalent group having a $C_5$-$C_{30}$ carbocyclic aromatic system, wherein the monovalent group may be a monocyclic or polycyclic group. In the polycyclic group, at least two rings included therein may be fused to each other. Examples of the unsubstituted $C_5$-$C_{30}$ aryl group may include phenyl, pentalenyl, indenyl, naphtyl, azulenyl, heptalenyl, indacenyl, acenaphtyl, fluorenyl, spiro-fluorenyl, phenalenyl, phenanthrenyl, anthryl, fluoranthenyl, triphenylenyl, pyrenyl, chrysenyl, naphthacenyl, picenyl, perylenyl, pentaphenyl, hexacenyl, and the like. A substituent of the substituted $C_5$-$C_{30}$ aryl group is described in the description for the "substituted A."

The unsubstituted $C_5$-$C_{30}$ aryloxy group denotes a monovalent group, to which carbon atoms of the $C_5$-$C_{30}$ aryl group are attached through an oxygen linking group (—O—). A substituent of the substituted $C_5$-$C_{30}$ aryloxy group is described in the description for the "substituted A."

The unsubstituted $C_5$-$C_{30}$ arylthio group denotes a monovalent group, to which carbon atoms of the $C_5$-$C_{30}$ aryl group are attached through a sulfur linking group (—S—). Examples of the unsubstituted $C_5$-$C_{30}$ arylthio group may include phenylthio, naphtylthio, indanylthio, and indenylthio. A substituent of the substituted $C_5$-$C_{30}$ arylthio group is described in the description for the "substituted A."

The unsubstituted $C_2$-$C_{30}$ heterocyclic group denotes a monocyclic or polycyclic group including at least one ring containing at least one heteroatom selected from the group consisting of N, O, P, and S. In the polycyclic group, at least two rings included therein may be fused to each other. Examples of the unsubstituted $C_2$-$C_{30}$ heterocyclic group may include pyrrolyl, imidazolyl, pyrazolyl, pyridinyl, pyrazinyl, pyrimidinyl, pyridazinyl, isoindolyl, indolyl, indazolyl, purinyl, quinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzooxazolyl, benzoimidazolyl, furanyl, benzofuranyl, thiophenyl, benzothiophenyl, thiazolyl, isothiazolyl, benzothiazolyl, isoxazolyl, oxazolyl, triazolyl, tetrazole, oxadiazolyl, triazinyl, benzooxazolyl, and the like. A substituent of the substituted $C_2$-$C_{30}$ heterocyclic group is described in the description for the "substituted A."

The unsubstituted $C_1$-$C_{30}$ alkylene group denotes a divalent group having a linear and chain structure, in which two hydrogen atoms are lacking alkane. Examples of the unsubstituted $C_1$-$C_{30}$ alkylene group may be understood with reference to the examples of the unsubstituted $C_1$-$C_{30}$ alkyl group. A substituent of the substituted $C_1$-$C_{30}$ alkylene group is described in the description for the "substituted A."

The unsubstituted $C_5$-$C_{30}$ arylene group may denote a divalent group having a $C_5$-$C_{30}$ carbocyclic aromatic system, wherein the divalent group may be a monocyclic or polycyclic group. Examples of the unsubstituted $C_5$-$C_{30}$ arylene group may be understood with reference to the examples of the unsubstituted $C_5$-$C_{30}$ aryl group. A substituent of the substituted $C_5$-$C_{30}$ arylene group is described in the description for the "substituted A."

The unsubstituted divalent $C_2$-$C_{30}$ heterocyclic group denotes a monocyclic or a polycyclic divalent group including at least one ring containing at least one heteroatom selected from the group consisting of N, O, P, and S and may be a monocyclic or a polycyclic group. Examples of the unsubstituted divalent $C_2$-$C_{30}$ heterocyclic group may be understood with reference to the examples of the unsubstituted $C_2$-$C_{30}$ heterocyclic group. A substituent of the substituted divalent $C_2$-$C_{30}$ heterocyclic group is described in the description for the "substituted A."

The condensed-cyclic compound represented by Formula 1 may be synthesized by using a well-known organic synthesis method. The synthesis method of the condensed-cyclic compound may be easily recognized by one of ordinary skill in the art with reference to Examples which will be described later.

According to another embodiment of the present invention, an organic light-emitting device includes a first electrode, a second electrode facing the first electrode, and at least one organic layer interposed between the first electrode and the second electrode, wherein the at least one organic layer includes the condensed-cyclic compound represented by Formula 1.

The condensed-cyclic compound represented by Formula 1 may be used in an organic light-emitting device. The condensed-cyclic compound represented by Formula 1 may excellently represent all colors such as red, green, blue, and white in an organic light-emitting device, lowers a driving voltage, increases efficiency of the organic light-emitting device, and improves the lifetime of organic light-emitting device.

The organic layer may be a hole injection layer or a hole transport layer in the organic light-emitting device. In this case, the condensed-cyclic compound represented by Formula 1 may be included as a material for forming a hole injection layer or a hole transport layer. The organic layer may be a functional layer having functions of both hole injection and hole transport. In this case, the condensed-cyclic compound represented by Formula 1 may be included as a material for forming such a single layer.

The organic light-emitting device may include a hole transport layer including the condensed-cyclic compound represented by Formula 1 or an emission layer including a fluorescent or phosphorescent host.

For example, the organic light-emitting device may have a structure including a first electrode/a hole injection layer/a hole transport layer including the condensed-cyclic compound represented by Formula 1/an emission layer/an electron transport layer/an electron injection layer/a second electrode. However, the present invention is not limited thereto.

Also, the organic layer may be an emission layer in an organic light-emitting device and thus the condensed-cyclic compound represented by Formula 1 may be included as a material for forming the emission layer. More specifically, the emission layer may only include the condensed-cyclic compound represented by Formula 1 or may further include another compound in addition to the condensed-cyclic compound represented by Formula 1.

For example, the condensed-cyclic compound represented by Formula 1 may be used as a fluorescent host or a phosphorescent host in the emission layer. In this case, the emission layer may further include a fluorescent dopant or a phosphorescent dopant. That is, the emission layer may include the condensed-cyclic compound represented by Formula 1 functioning as a fluorescent host and a fluorescent dopant or may include the condensed-cyclic compound represented by Formula 1 functioning as a phosphorescent host and a phosphorescent dopant. Also, the condensed-cyclic compound represented by Formula 1 may be used as a fluorescent dopant of the emission layer. In this case, the condensed-cyclic compound represented by Formula 1 may further include a fluorescent host or a phosphorescent host. That is, the emission layer may include the condensed-cyclic compound represented by Formula 1 functioning as a fluorescent dopant, a phosphorescent host, or a fluorescent host.

The organic light-emitting device may include at least one selected from the group consisting of a hole injection layer, a hole transport layer, an electron blocking layer, a hole blocking layer, an electron transport layer, and an electron injection layer between the first electrode and the second electrode, in addition to the emission layer.

The at least one layer interposed between the first electrode and the second electrode may be formed by deposition or a wet process. For example, at least one selected from the group consisting of a hole injection layer, a hole transport layer, an emission layer, a hole blocking layer, an electron transport layer, and an electron injection layer between the first electrode and the second electrode may be formed by deposition or a wet process.

In the specification, "wet process" is a process for providing a mixture obtained by mixing a predetermined material and a predetermined solvent to a predetermined substrate, drying and/or thermal treating the predetermined substrate so as to remove at least part of the predetermined solvent, and thereby forming a film including the predetermined material on the substrate.

An organic layer including the condensed-cyclic compound represented by Formula 1 may be formed by a general vacuum deposition of a wet process.

For example, the condensed-cyclic compound represented by Formula 1 and the mixture including the solvent are provided to a hole transport layer region by using spin ti coating, spraying, inkjet printing, dipping, casting, gravure coating, bar coating, roll coating, wirebar coating, screen coating, flexo coating, offset coating, or laser transferring and then the mixture provided to the hole transport layer region is dried and/or heat treated so as to remove at least part of the solvent. Thus, the hole transport layer including the condensed-cyclic compound represented by Formula 1 may be formed.

Also, a layer including the condensed-cyclic compound represented by Formula 1 may be formed on the base film by using a wet process and the layer may be transferred on the hole transport layer region by laser transferring using laser.

FIG. 1 is a cross-sectional view of an organic light-emitting device 10 according to an embodiment of the present invention. Hereinafter, a structure and a manufacturing method of the organic light-emitting device 10 will be described with reference to FIG. 1.

The organic light-emitting device 10 includes a substrate 11, a first electrode 12, a hole injection layer 13, a hole transport layer 14, an emission layer 15, an electron transport layer 16, an electron injection layer 17, and a second layer 18 sequentially in this order.

The substrate 11 may be a substrate used in a general organic light-emitting device and may be, for example, a glass substrate or a transport plastic substrate having excellent mechanical strength, thermal stability, transparency, surface smoothness, easy-handling, and waterproofness.

The first electrode 12 may be formed by providing a first electrode material on the substrate 11 using deposition or sputtering. When the first electrode 12 is an anode, the first electrode material may be selected from materials having a high work function so as to facilitate hole injection. The first electrode 12 may be a reflective electrode or a transmissive electrode. Examples of the first electrode material may include indium-tin oxide (ITO), Indium-zinc-oxide (IZO), tin oxide ($SnO_2$), and zinc oxide (ZnO). Also, when magnesium (Mg), aluminum (Al), aluminum-lithium (Al—Li), calcium (Ca), magnesium-indium (Mg—In), or magnesium-silver (Mg—Ag) is used, the first electrode 12 may be formed as a reflective electrode. The first electrode 12 may include two different materials. The structure of the first electrode 12 may vary and, for example, the first electrode 12 may be formed to have a two-layered structure including two different materials.

The hole injection layer 13 is formed on the first electrode 12.

The hole injection layer 13 may be formed on the first electrode 12 by using various methods such as vacuum deposition, a wet process, or laser transferring.

When the hole injection layer 13 is formed by using a vacuum deposition, the deposition condition may vary according to a compound used as a material for a hole injection layer, a structure of a desired hole injection layer, and thermal characteristics. For example, the deposition condition may be, but is not limited to, deposition temperature of about 100 to about 500° C., a degree of vacuum of about $10^{-8}$ to about $10^{-3}$ torr, and deposition speed of about 0.01 to about 100 Å/sec.

When the hole injection layer 13 is formed by using spin coating as a wet process, the coating condition may vary according to a compound used as a material for a hole injection layer, a structure of a desired hole injection layer, and thermal characteristics. For example, the coating condition may be, but is not limited to, coating speed of about 2000 rpm to about 5000 rpm and heat treatment temperature for removing a solvent after coating of about 80 to about 200° C.

The condensed-cyclic compound may be used as the material for a hole injection layer. Also, the material for a hole injection layer may include at least one selected from the group consisting of the condensed-cyclic compound and a well-known material for a hole injection layer and may include, for example, a phthalocyanine compound such as copper phthalocyanine, m-MTDATA (refer to Formula below), TDATA (refer to Formula below), 2-TDATA (refer to Formula below), Polyaniline/Dodecylbenzenesulfonic acid (Pani/DBSA), Poly(3,4-ethylenedioxythiophene)/Poly(4-styrenesulfonate) (PEDOT/PSS), Polyaniline/Camphor sulfonicacid (Pani/CSA), or Polyaniline/Poly(4-styrenesulfonate) (PAN1/PSS). However, the present invention is not limited thereto.

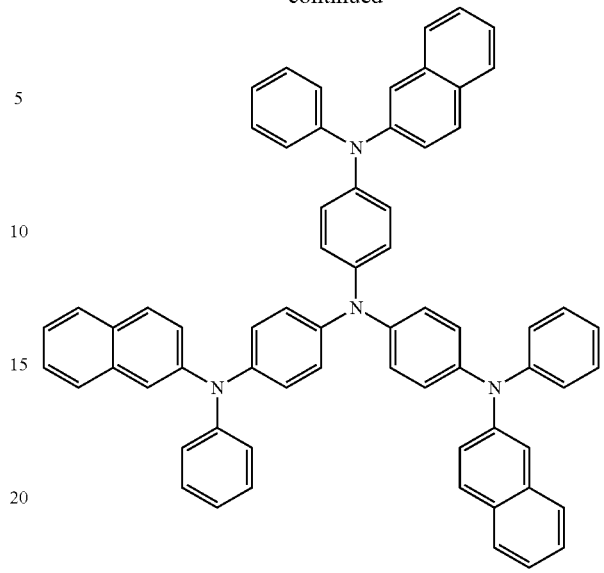

2-TNATA

A thickness of the hole injection layer 13 may be about 100 Å to about 10000 Å, for example, about 100 Å to about 1000 Å. When the thickness of the hole injection layer 13 is in the above range, satisfiable hole injection characteristics may be obtained without a substantial increase of a driving voltage.

Then, the hole transport layer 14 is formed on the hole injection layer 13 by using vacuum deposition, a wet process, and laser transferring. When the hole transport layer 14 is formed by vacuum deposition and spin coating, the deposition condition and coating condition may vary according to a used compound. However, in general, the conditions may be almost similar to the condition for forming the hole injection layer 13.

The condensed-cyclic compound represented by Formula 1 may be used as a material for a hole transport layer. Also, the hole transport layer 14 may further include a well-known material for a hole transport layer, for example, TPD (refer to Formula below) and NPB (refer to Formula below).

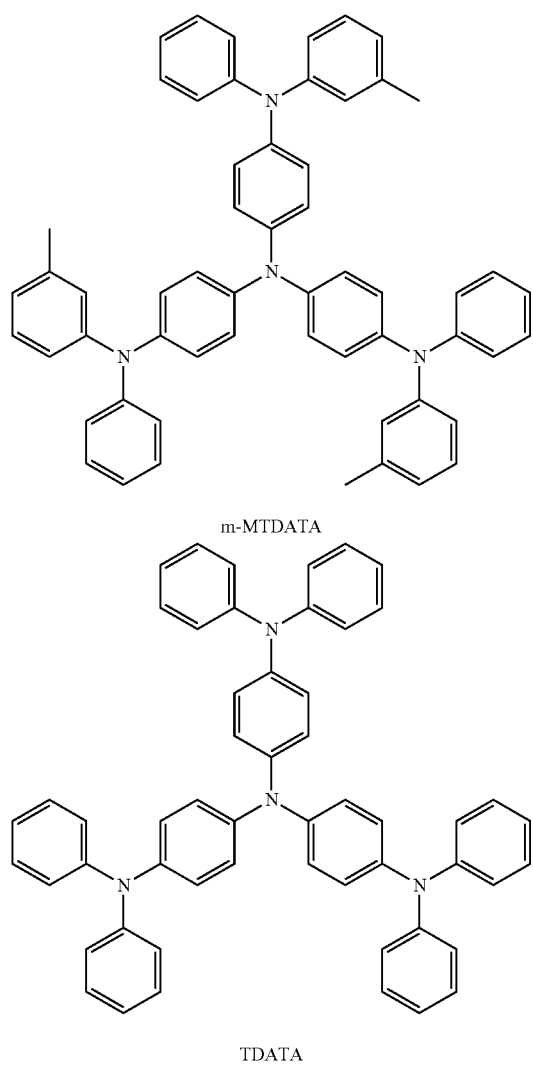

m-MTDATA

TDATA

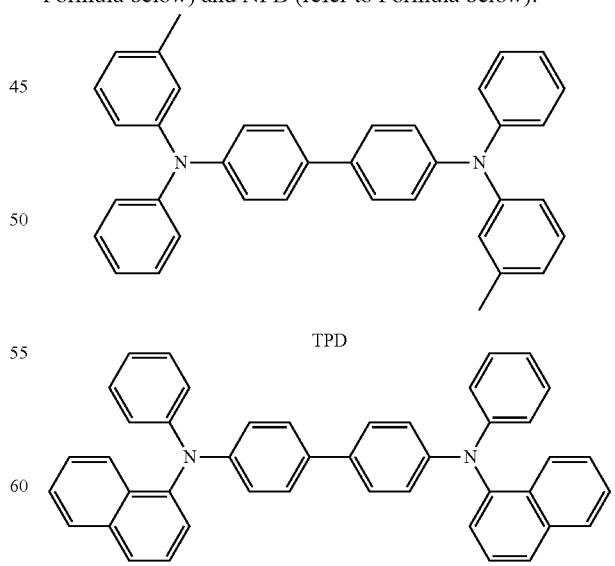

TPD

NPB

A thickness of the hole transport layer 14 may be about 50 Å to about 1000 Å, for example, about 100 Å to about 800 Å. When the thickness of the hole transport layer 14 is in the above range, satisfiable hole transport characteristics may be obtained without a substantial increase of a driving voltage.

Instead of the hole injection layer 13 and the hole transport layer 14, a function layer (not illustrated) simultaneously having a hole injection function and a hole transport function may be formed. A material for forming the function layer simultaneously having a hole injection function and a hole transport function may be selected from well-known materials.

At least one selected from the group consisting of the hole injection layer 13, the hole transport layer 14, and the functional layer simultaneously having a hole injection function and a hole transport function may further include a charge-generation material for improving conductivity of a layer, in addition to the condensed-cyclic compound represented by Formula 1, a well-known hole injection material, and a well-known hole transport material.

Examples of the charge-generation material may include a p-dopant. Examples of the p-dopant may include, but are not limited to, a quinone derivative such as tetracyanoquinonedimethan (TCNQ) or 2,3,5,6-tetrafluoro-tetracyano-1,4-benzonquinonedimethane (F4TCNQ); a metal oxide such as a tungsten oxide or a molybdenum oxide; and a cyano group containing a compound such as hexanitrile hexaazatriphenylene.

When the hole injection layer 13, the hole transport layer 14, or the functional layer simultaneously having a hole injection function and a hole transport function further includes the charge-generation material, the charge-generation material is homogeneously or non-homogeneously dispersed in the layers.

The emission layer 15 may be formed on the hole transport layer 14 or the functional layer simultaneously having a hole injection function and a hole transport function by using vacuum deposition, a wet process, or laser transferring. When the emission layer 15 is formed by vacuum deposition and spin coating, the deposition condition may vary according to a used compound. However, in general, the conditions may be almost similar to the condition for forming the hole injection layer 13.

The emission layer 15 may include at least one selected from the group consisting of the condensed-cyclic compound of Formula 1 and well-known phosphorescent host, fluorescent host, phosphorescent dopant, and fluorescent dopant. When the emission layer 15 includes the condensed-cyclic compound represented by Formula 1, the condensed-cyclic compound may function as a phosphorescent host, a fluorescent host, a phosphorescent dopant, or a fluorescent dopant.

Examples of the well-known host may include 4,4'-N,N'-dicarbazole-biphenyl (CBP), 9,10-di-naphthalene-2-yl-anthracene (AND, refer to Formula below), TPBI (refer to Formula below), TBADN (refer to Formula below), E3 (refer to Formula below). However, the present invention is not limited thereto.

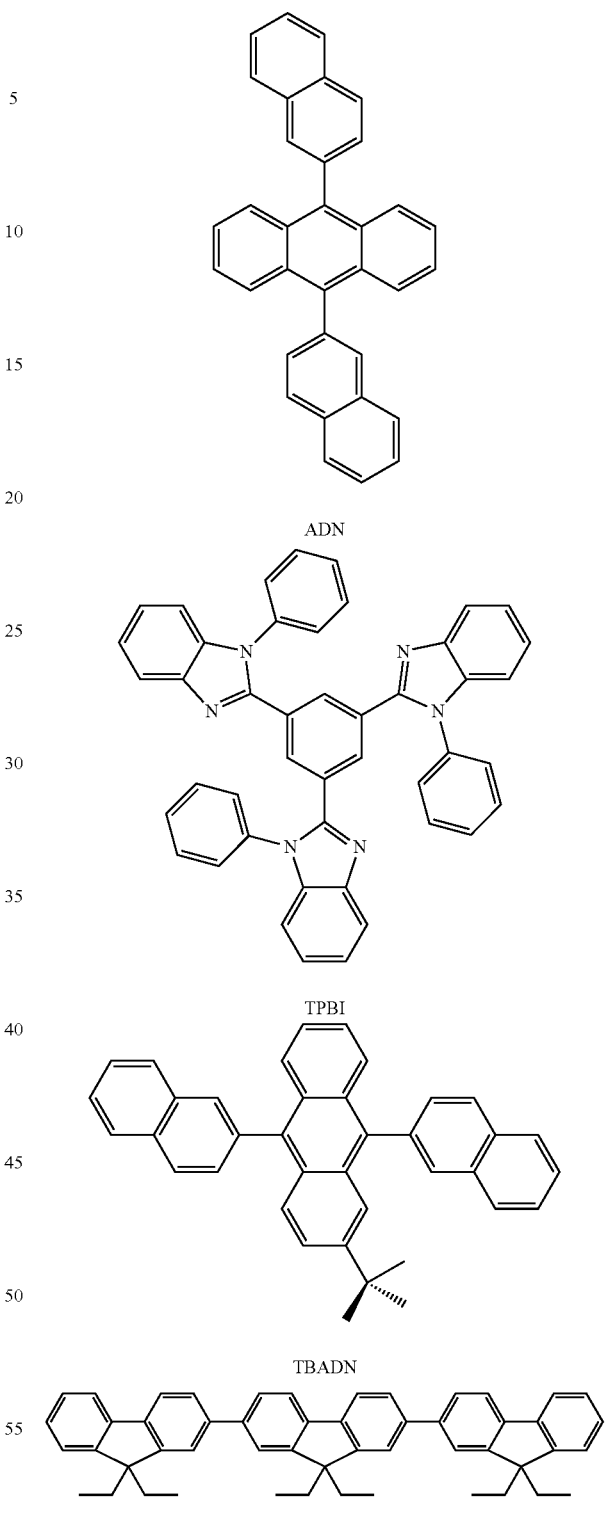

ADN

TPBI

TBADN

E3

At least one of the fluorescent dopant and the phosphorescent dopant may be used as a dopant. The phosphorescent dopant may be an organic metal complex including Ir, Pt, Os, Re, Ti, Zr, Hf, or combinations including at least two of Ir, Pt, Os, Re, Ti, Zr, and Hf. However, the present invention is not limited thereto.

As a red dopant, PtOEP (refer to Formula below), Ir (piq)$_3$ (refer to Formula below), or Btp$_2$Ir(acac) (refer to Formula below) may be used. However, the present invention is not limited thereto.

or Ir(mpyp)$_3$ (refer to Formula below) may be used. However, the present invention is not limited thereto.

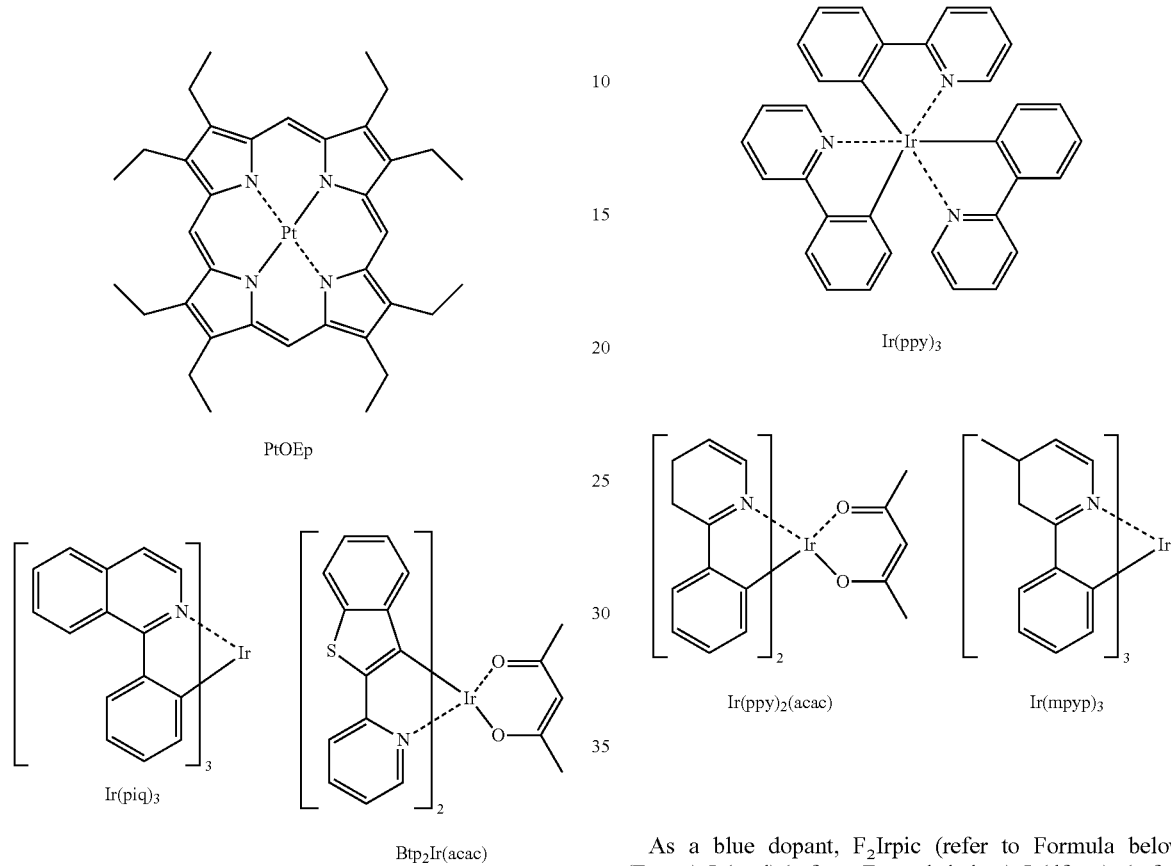

As a green dopant, Ir(ppy)$_3$ (ppy=phenyl-pyridines, refer to Formula below), Ir(ppy)$_2$(acac) (refer to Formula below), As a blue dopant, F$_2$Irpic (refer to Formula below), (F$_2$ppy)$_2$Ir(tmd) (refer to Formula below), Ir(dfppz)$_3$ (refer to Formula below), DPVBi (refer to Formula below), 4,4'-bis(4-diphenylaminosteril) biphenyl (DPAVBi, refer to Formula below), or 2,5,8,11-tetra-tert-butylpherylene (TBPe, refer to Formula below) may be used. However, the present invention is not limited thereto.

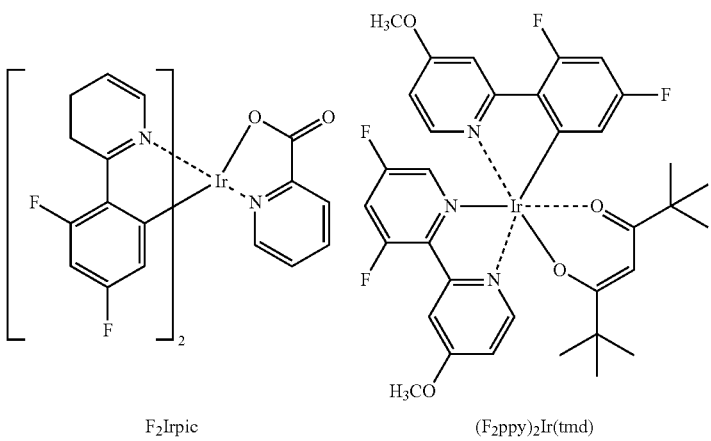

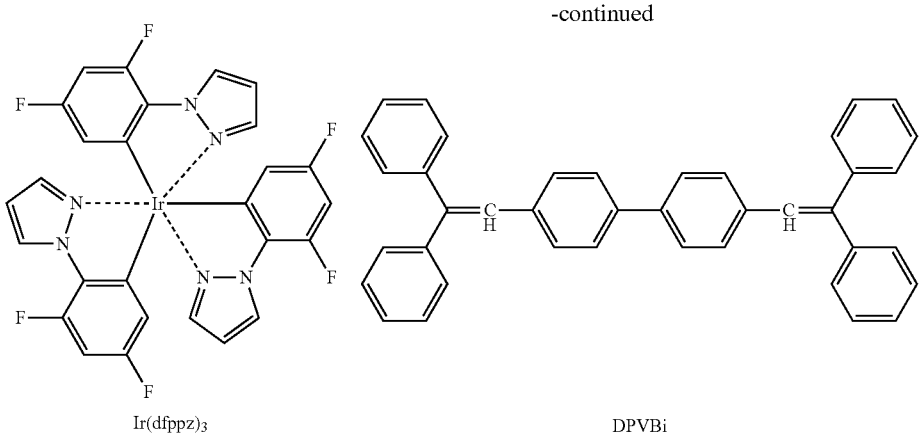

Ir(dfppz)₃

DPVBi

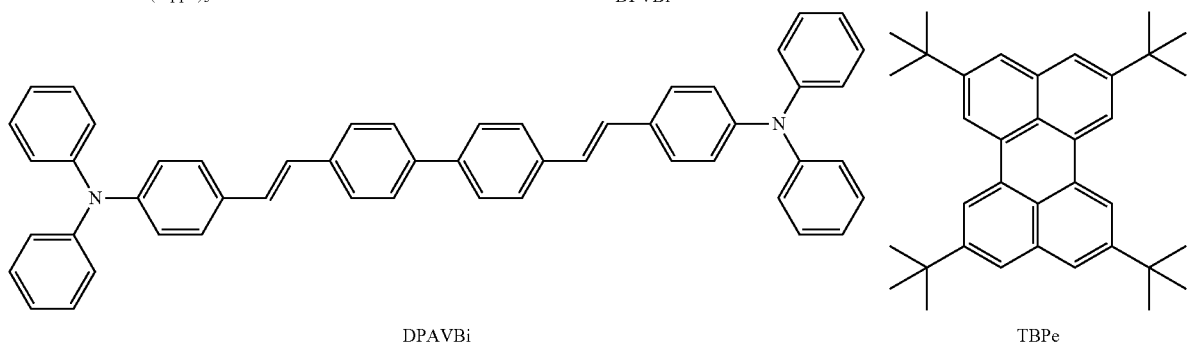

DPAVBi

TBPe

When the emission layer 15 includes a host and a dopant, an amount of the dopant may be generally in the range of about 0.01 to about 15 parts by weight based on 100 parts by weight of the host. However, the present invention is not limited thereto.

A thickness of the emission layer 15 may be about 100 Å to about 1000 Å, for example, about 200 Å to about 600 Å. When the thickness of the emission layer 15 is in the above range, excellent emission characteristic may appear without a substantial increase of a driving voltage.

When the phosphorescent dopant is included in the emission layer 15, a hole blocking layer (not illustrated) may be formed between the emission layer 15 and the hole transport layer 16 by using vacuum deposition, a wet process, or laser transferring so as to prevent triplet excitons or holes from being diffused to the electron transport layer 16.

When the hole blocking layer is formed by using vacuum deposition and spin coating, the conditions thereof may vary according to a used compound. However, in general, the conditions may be almost similar to the condition for forming the hole injection layer 13. A well-known hole blocking material may be used. Examples of the well-known hole blocking material may include an oxadiazole deriative, a triazole derivative, and a phenanthroline derivative.

A thickness of the hole blocking layer may be about 50 Å to about 1000 Å, for example, about 100 Å to about 300 Å. When the thickness of the hole blocking layer is in the above range, excellent hole blocking characteristic may appear without a substantial increase of a driving voltage.

Then, the electron transport layer 16 is formed by using vacuum deposition, a wet process, or laser transferring. When the electron transport layer 16 is formed by using vacuum deposition or spin coating, the conditions thereof may vary according to a used compound. However, in general, the conditions may be almost similar to the condition for forming the hole injection layer 13. A material for forming the electron transport layer 16 is used to stably transport electrons injected from a cathode and may include a well-known transport material. Examples of the well-known transport material may include a quinoline derivative, in particular, tris(8-quinolinolate)aluminum (Alq₃), TAZ (refer to Formula below), Balq (refer to Formula below), beryllium bis benzoquinolin-10-olate (Bebq₂). However, the present invention is not limited thereto.

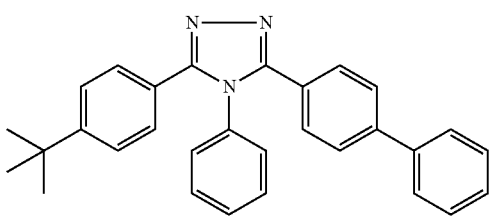

TAZ

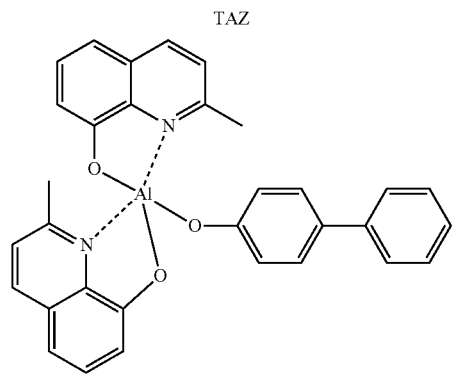

BAlq

A thickness of the electron transport layer 16 may be about 100 Å to about 1000 Å, for example, about 150 Å to about 500 Å. When the thickness of the electron transport layer 16 is in the above range, excellent electron transport characteristic may be obtained without a substantial increase of a driving voltage.

Also, the electron transport layer 16 may include an electron transport organic compound and a metal-containing material. Examples of the electron transport organic compound may include, but are not limited to, 9,10-di(naphthalene-2-yl)anthracene (AND); and an anthracene-based compound such as a compound 301 or 302 below:

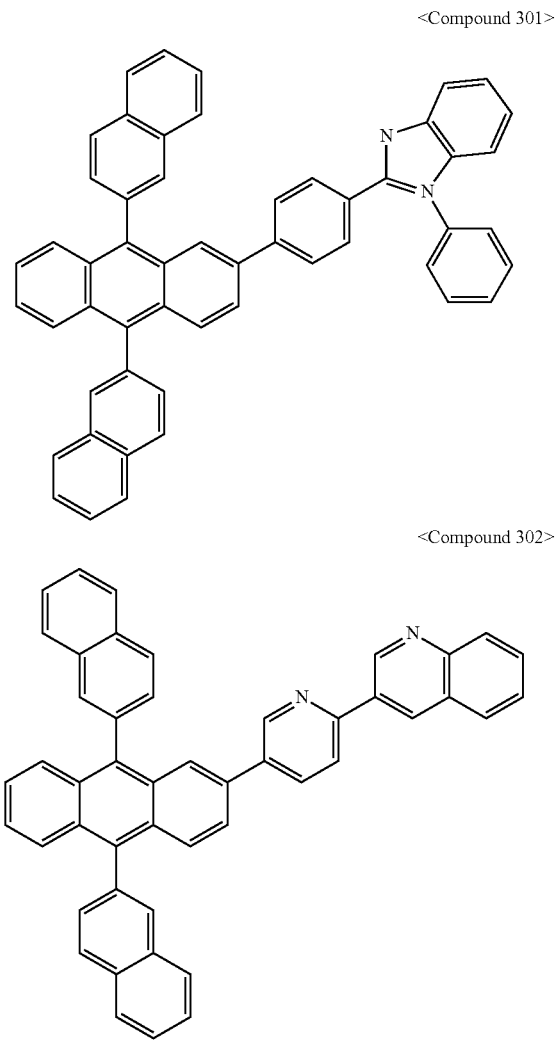

<Compound 301>

<Compound 302>

The metal-containing material may include a Li complex. Examples of the Li complex may include, but are not limited to, lithium quinolate (LiQ) or compound 303 below:

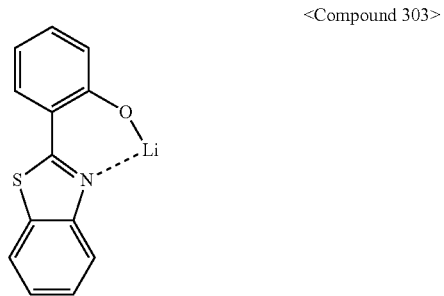

<Compound 303>

Also, the electron injection layer 17, which facilitates electron injection from a cathode, may be formed on the electron transport layer 16. A material for forming the electron injection layer 17 may include a well-known arbitrary material for forming the electron injection layer, such as LiF, NaCl, CsF, $Li_2O$, or BaO.

The deposition condition of the electron injection layer 17 may vary according a used compound. However, in general, the condition may be almost similar to the condition for forming the hole injection layer 13.

A thickness of the electron injection layer 17 may be about 1 Å to about 100 Å, for example, about 3 Å to about 90 Å. When the thickness of the electron injection layer 17 is in the above range, satisfiable hole injection characteristics may be obtained without a substantial increase of a driving voltage.

The second electrode 18 as a transmissive electrode may be formed on the electron injection layer 17. The second electrode 18 may be a cathode, which is an electrode injection electrode. Here, a metal for forming the second electrode 18 may include a metal having low work function, an alloy, an electric conducting compound, and mixtures thereof. More specifically, the transmissive electrode may be obtained by forming a thin film by using lithium (Li), magnesium (Mg), aluminum (Al), aluminum-lithium (Al—Li), calcium (Ca), magnesium-indium (Mg—In), or magnesium-silver (Mg—Ag). In order to obtain a top-emission light-emitting device, the transmissive electrode may be formed by using ITO or IZO.

According to another embodiment of the present invention, a flat panel display apparatus includes an organic light-emitting device including a transistor including a source electrode, a drain electrode, a gate, and an active layer, and an organic layer including the to condensed-cyclic compound represented by Formula 1 above, wherein in the organic light-emitting device, the first electrode is electrically connected to the source electrode or the drain electrode.

The organic light-emitting device may be included in the flat panel display apparatus including the transistor. The active layer of the transistor may vary and may be, for example, an amorphous silicon layer, a crystallized silicon layer, an organic semiconductor layer, or an oxide semiconductor layer.

Hereinafter, an organic light-emitting device according to the present invention will be described more specifically with reference to the following Synthesis Examples and Examples. The following Synthesis Examples and Examples are for illustrative purposes and are not intended to limit the scope of the invention.

EXAMPLES

Synthesis Example 1

Synthesis of Compound 1

Compound 1 was manufactured through Reaction Formula 1 below:

<Reaction Formula 1>

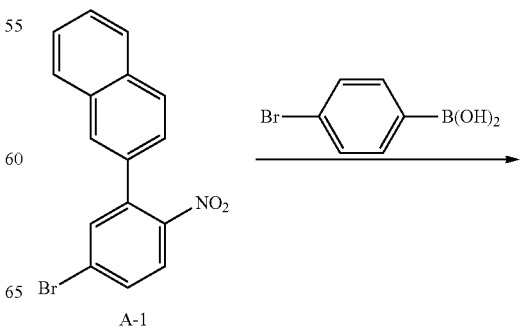

A-1

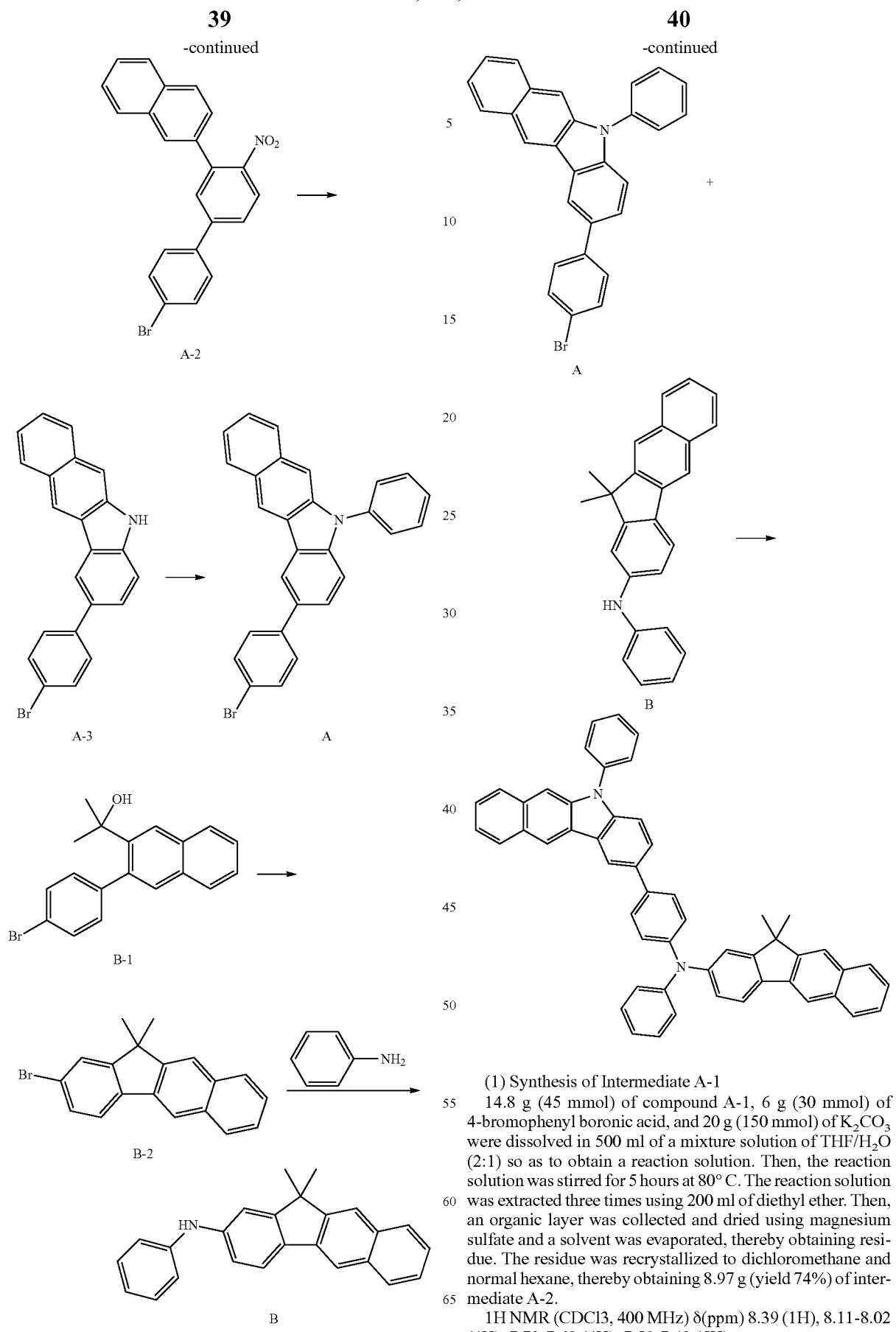

(1) Synthesis of Intermediate A-1

14.8 g (45 mmol) of compound A-1, 6 g (30 mmol) of 4-bromophenyl boronic acid, and 20 g (150 mmol) of $K_2CO_3$ were dissolved in 500 ml of a mixture solution of $THF/H_2O$ (2:1) so as to obtain a reaction solution. Then, the reaction solution was stirred for 5 hours at 80° C. The reaction solution was extracted three times using 200 ml of diethyl ether. Then, an organic layer was collected and dried using magnesium sulfate and a solvent was evaporated, thereby obtaining residue. The residue was recrystallized to dichloromethane and normal hexane, thereby obtaining 8.97 g (yield 74%) of intermediate A-2.

1H NMR (CDCl3, 400 MHz) δ(ppm) 8.39 (1H), 8.11-8.02 (4H), 7.73-7.68 (4H), 7.59-7.43 (5H)

(2) Synthesis of Intermediate A-3

154 mmol of triethylphosphate was added to 8.97 g (22 mmol) of compound A-2 so as to obtain a reaction mixture. The reaction mixture was heated and refluxed for 12 hours. After the reaction was completed, an excessive amount of triethylphosphate was distilled. Distilled water and methanol were added to residue to generate a solid. The generated solid was filtered and was recrystallized to normal hexane and dichloromethane. Accordingly, 4.9 g (yield 60%) of a product was obtained.

1H NMR (CDCl3, 400 MHz) δ(ppm) 8.23 (2H), 8.03 (1H), 7.89 (1H), 7.74-7.62 (5H), 7.53 (3H), 7.28 (1H)

(3) Synthesis of Intermediate A 32.8 g (88.0 mmol) of intermediate A-3 and 13.1 g (64.2 mmol) of iodine benzene were dissolved in xylene, as a solvent, so as to form a mixture solution. Then, 1.5 ml (6.1 mmol) of P(t-Bu)$_3$, 0.25 g (1.2 mmol) of palladium acetate, and 40 g (476 mmol) of solid state K$_3$PO$_4$ were added to the mixture solution so as to obtain a reaction mixture. Then, the mixture solution was heated and refluxed. After 12 hours, the reaction mixture was cooled down to room temperature and 500 ml of water was slowly added to the cooled reaction mixture. A solid product was filtered, washed three times using distilled water, and dried using anhydrous magnesium sulfate. Then, the solvent was removed, thereby obtaining a solid product. The solid product was recrystallized to normal hexane and dichloromethane, thereby obtaining 26.4 g (67%) of intermediate A.

1H NMR (CDCl3, 400 MHz) δ(ppm) 8.23 (2H), 8.19 (1H), 8.03 (1H), 7.91-7.87 (2H), 7.75-7.58 (8H), 7.51-7.42 (4H)

(4) Synthesis of Intermediate B 10.2 g (30 mmol) of intermediate B-1 was melted in dried chloroform and then 5.1 g (36 mmol) of 3-boron trifluoride ether (boron trifluoride-diethyl etherate) was slowly added for 10 minutes, thereby obtaining a mixture solution. The temperature of the mixture solution increased to 50° C. and the mixture solution was stirred for 2 hours. The mixture solution was again cooled down to room temperature and distilled water is added to the mixture solution, and the mixture solution was extracted three times using diethyl ether, thereby obtaining an organic layer. The organic layer was dried using anhydrous magnesium sulfate. A solvent was removed and concentrated residue was separated and purified using silica gel chromatography, thereby obtaining 5.1 g of intermediate B-2 (yield 53%). 3.2 g (10 mmol) of intermediate B-2, 0.91 ml (10 mmol) of aniline, 1.4 g (15 mmol) of t-BuONa, 8 g 0.18 g (0.2 mmol) of Pd2(dba)$_3$, and 0.04 g (0.2 mmol) of P(t-Bu)$_3$ were melted in 50 ml of toluene and then stirred for 3 hours at 90° C. so as to obtain a reaction solution. After the reaction was completed, the reaction solution was cooled down to room temperature and was extracted three times using 40 ml of distilled water and diethyl ether. An organic layer is dried using anhydrous magnesium sulfate and a solvent was removed, thereby obtaining residue. The residue was separated and purified using silica gel column chromatography, thereby obtaining 2.08 g of intermediate (yield 62%).

1H NMR (CDCl3, 400 MHz) δδ(ppm) 8.43 (1H), 8.21 (2H), 7.98 (1H), 7.73-7.62 (3H), 7.31-7.28 (4H), 7.03-6.97 (3H), 10.79 (6H)

(5) Synthesis of Compound 1

4.48 g (10 mmol) of intermediate A, 3.4 g (10 mmol) of compound B, 1.4 g (15 mmol) of t-BuONa, 8 g 0.18 g (0.2 mmol) of Pd$_2$(dba)$_3$, and 0.04 g (0.2 mmol) of P(t-Bu)$_3$ were melted in 50 ml of toluene and then stirred for 3 hours at 90° C. so as to obtain a reaction solution. After the reaction was completed, the reaction solution was cooled down to room temperature and was extracted three times using 40 ml of distilled water and diethyl ether. An organic layer is dried using anhydrous magnesium sulfate and a solvent was removed, thereby obtaining residue. The residue was separated and purified using silica gel column chromatography, thereby obtaining 5.5 g of compound 1 (yield 62%).

1H NMR (CDCl3, 400 MHz) δ(ppm) 8.43 (1H), 8.21 (2H), 7.02 (2H), 7.92-7.85 (3H), 7.68-7.52 (12H), 7.49-7.27 (6H), 7.09-6.83 (6H), 1.79 (6H)

Example 1

As an anode, 15 Ω/cm$^2$ (1200 Å) of an ITO glass substrate from Corning Co., Ltd. was cut into 50 mm×50 mm×0.7 mm, was ultrasonic washed for 5 minutes respectively using isopropyl alcohol and purified water, and was UV-ozone washed for 15 minutes. 4,4',4"-tris[3-methylphenyl(phenyl)-amino] triphenylamine (m-MTDATA) was vacuum deposited on the substrate so as to form a hole injection layer having a thickness of 600 Å. Then, compound 1 was vacuum deposited on the hole injection layer, thereby forming a hole transport layer having a thickness of 300 Å. IDE215 (Idemitsu Co., Ltd.) as a blue fluorescent host and IDE118 (Idemitsu Co., Ltd.) as a blue fluorescent dopant were simultaneously deposited on the hole transport layer by a weight ratio of 97:3, thereby forming an emission layer having a thickness of 2001. Aluminum tris(8-hydroxyquinoline) was vacuum deposited on the emission layer, thereby forming an electron transport layer having a thickness of 300 Å. LiF was vacuum deposited on the electron transport layer so as to form an electron injection layer having a thickness of 10 Å and then Al was vacuum deposited on the electron injection layer so as to form a cathode having a thickness of 3000 Å. Therefore, an organic light-emitting device was completely manufactured.

The organic light-emitting device had a current density of 100 mA/cm$^2$, a driving voltage of 6.63 V, color coordinates of (0.143, 0.241), and emission efficiency of 7.11 cd/A.

Synthesis Example 2

Synthesis of Compound 2

Compound 2 was manufactured through Reaction Formula 2 below:

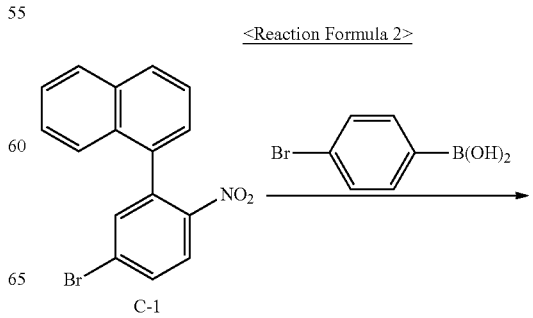

<Reaction Formula 2>

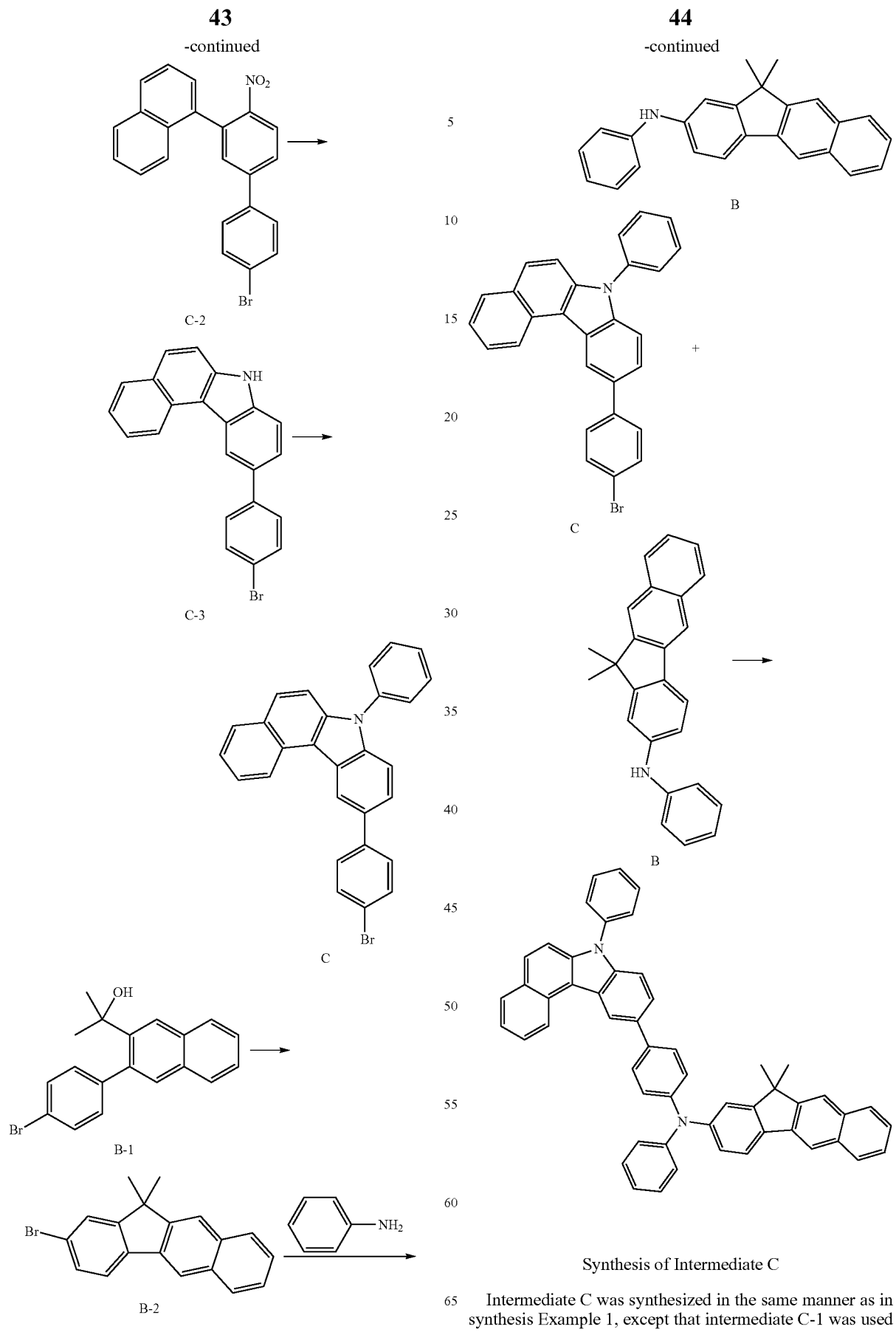
Synthesis of Intermediate C
Intermediate C was synthesized in the same manner as in synthesis Example 1, except that intermediate C-1 was used instead of intermediate A-1.

(2) Synthesis of Compound 2

Compound 2 having a yield of 78% was obtained by performing a coupling reaction in the same manner as in Synthesis Example 1 by using intermediate C, instead of intermediate A.

1H NMR (CDCl3, 400 MHz) δ(ppm) 8.64 (1H), 8.36 (1H), 8.21 (1H), 8.08-7.83 (6H), 7.73-7.48 (13H), 7.33 (2H), 7.21 (2H), 6.97-4.79 (6H), 1.79 (6H)

Example 2

An organic light-emitting device was completely manufactured in the same manner as in Example 1, except that compound 2 was used instead of compound 1 when forming the hole transport layer.

The organic light-emitting device had a current density of 100 mA/cm$^2$, a driving voltage of 6.75 V, color coordinates of (0.143, 0.242), and emission efficiency of 7.34 cd/A.

Synthesis Example 3

Synthesis of Compound 3

Compound 3 was manufactured through Reaction Formula 3 below:

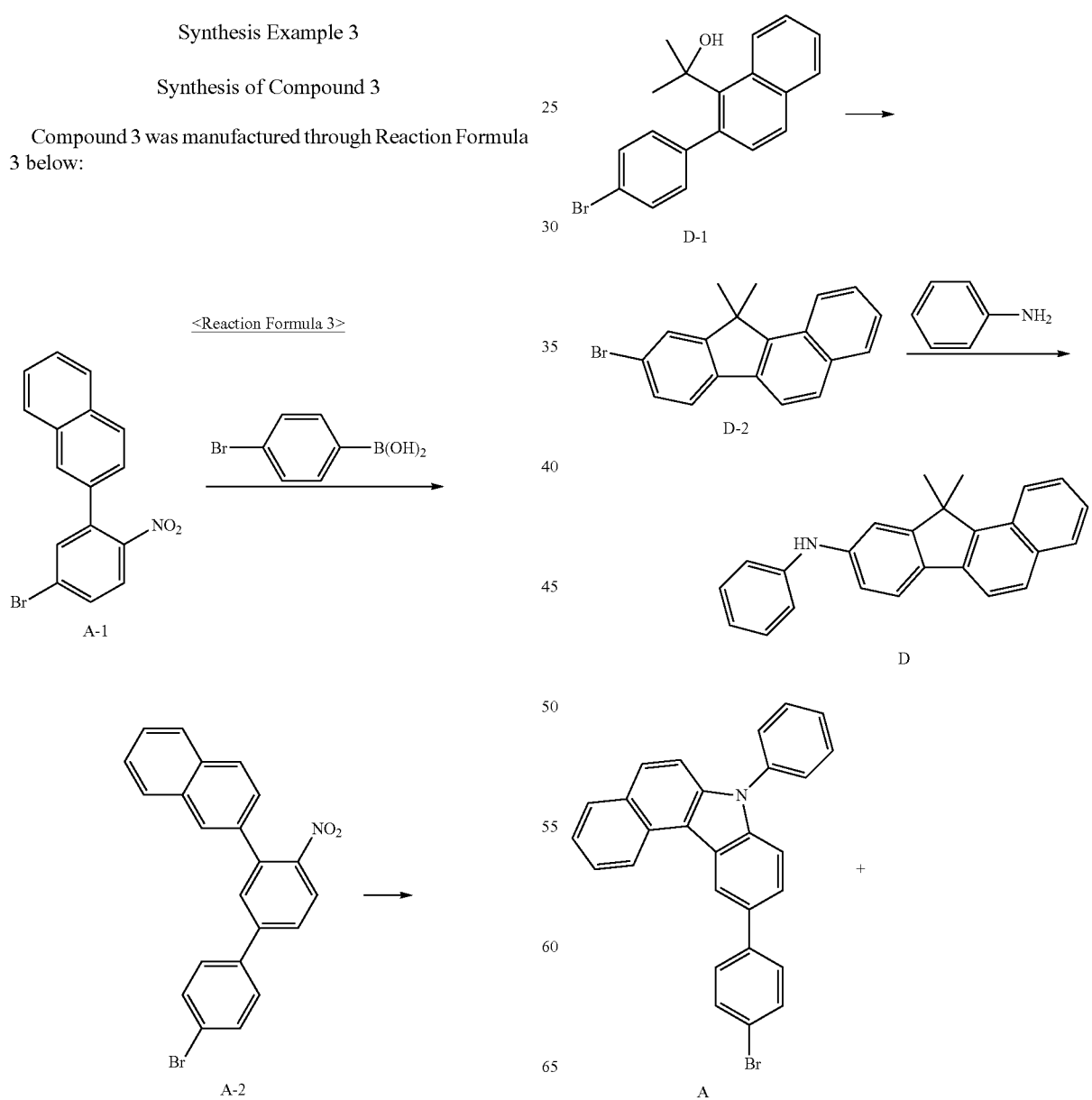

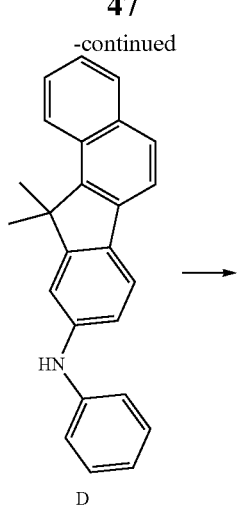

D

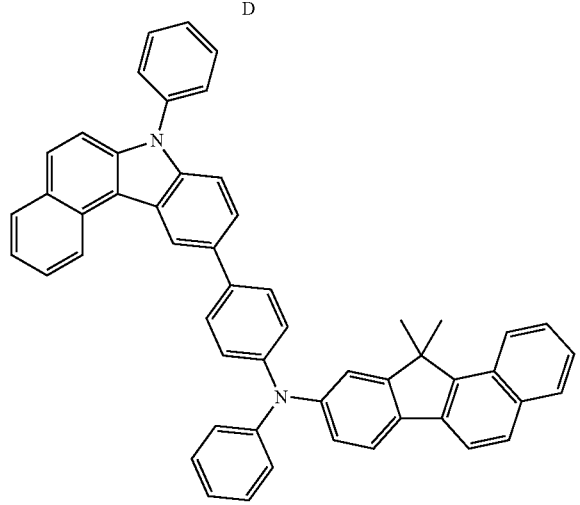

Synthesis of Intermediate D

Intermediate D was synthesized in the same manner as in synthesis Example 1, except that intermediate D-1 was used instead of intermediate B-1.

(2) Synthesis of Compound 3

Compound 3 having a yield of 81% was obtained by performing a coupling reaction in the same manner as in Synthesis Example 1 by using intermediate D, instead of intermediate B.

1H NMR (CDCl3, 400 MHz) δ(ppm) 8.64 (1H), 8.34 (2H), 8.11-7.75 (8H), 7.70-7.56 (12H), 7.28 (2H), 6.83 (2H), 6.73-6.64 (5H), 10.79 (6H)

Example 3

An organic light-emitting device was completely manufactured in the same manner as in Example 1, except that compound 3 was used instead of compound 1 when forming the hole transport layer.

The organic light-emitting device had a current density of 100 mA/cm$^2$, a driving voltage of 6.59 V, color coordinates of (0.143, 0.242), and emission efficiency of 7.21 cd/A.

Synthesis Example 4

Synthesis of Compound 4

Compound 4 was obtained in the same manner as in Synthesis Example 1 and a yield thereof was 81%.

1H NMR (CDCl3, 400 MHz) δ(ppm) 8.64 (1H), 8.34 (2H), 8.11-7.75 (8H), 7.70-7.56 (12H), 7.28 (2H), 6.83 (2H), 6.73-6.64 (5H), 1.79 (6H)

Example 4

An organic light-emitting device was completely manufactured in the same manner as in Example 1, except that compound 4 was used instead of compound 1 when forming the hole transport layer.

The organic light-emitting device had a current density of 100 mA/cm$^2$, a driving voltage of 6.69 V, color coordinates of (0.143, 0.241), and emission efficiency of 7.09 cd/A.

Synthesis Example 5

Synthesis of Compound 5

Compound 5 was obtained in the same manner as in Synthesis Example 1 and a yield thereof was 67%.

1H NMR (CDCl3, 400 MHz) δ(ppm) 8.36 (3H), 8.15 (2H), 7.91 (2H), 7.63-7.59 (2H), 7.53-7.43 (17H), 6.83-6.69 (6H), 1.79 (6H)

Example 5

An organic light-emitting device was completely manufactured in the same manner as in Example 1, except that compound 5 was used instead of compound 1 when forming the hole transport layer.

The organic light-emitting device had a current density of 100 mA/cm$^2$, a driving voltage of 6.78 V, color coordinates of (0.144, 0.241), and emission efficiency of 7.28 cd/A.

Comparative Example 1

An organic light-emitting device was completely manufactured in the same manner as in Example 1, except that 4,4'-bis[N-4,4'-bis[N-(1-naphtyl)-N-phenylamino]biphenyl (NPB) was used instead of compound 1 when forming the hole transport layer.

The organic light-emitting device had a current density of 100 mA/cm$^2$, a driving voltage of 7.82 V, color coordinates of (0.143, 0.242), and emission efficiency of 5.72 cd/A.

Comparative Synthesis Example 2

Synthesis of Compound 202

Compound 202 was manufactured through Reaction Formula 4 below:

<Reaction Formula 4>

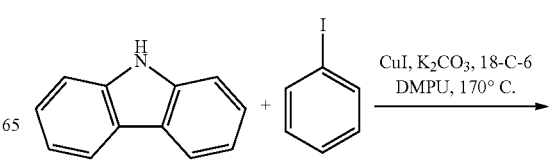

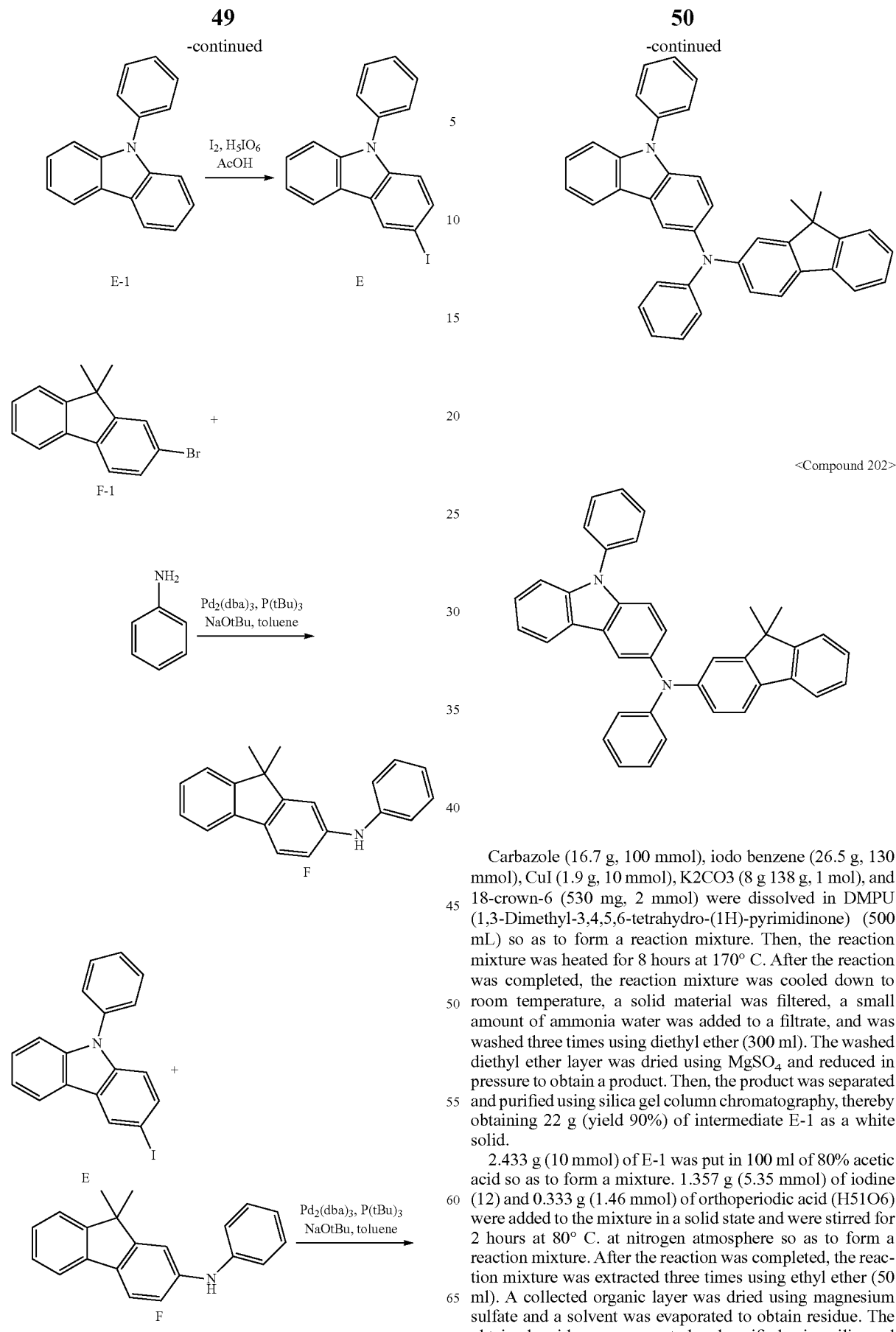

Carbazole (16.7 g, 100 mmol), iodo benzene (26.5 g, 130 mmol), CuI (1.9 g, 10 mmol), K2CO3 (8 g 138 g, 1 mol), and 18-crown-6 (530 mg, 2 mmol) were dissolved in DMPU (1,3-Dimethyl-3,4,5,6-tetrahydro-(1H)-pyrimidinone) (500 mL) so as to form a reaction mixture. Then, the reaction mixture was heated for 8 hours at 170° C. After the reaction was completed, the reaction mixture was cooled down to room temperature, a solid material was filtered, a small amount of ammonia water was added to a filtrate, and was washed three times using diethyl ether (300 ml). The washed diethyl ether layer was dried using $MgSO_4$ and reduced in pressure to obtain a product. Then, the product was separated and purified using silica gel column chromatography, thereby obtaining 22 g (yield 90%) of intermediate E-1 as a white solid.

2.433 g (10 mmol) of E-1 was put in 100 ml of 80% acetic acid so as to form a mixture. 1.357 g (5.35 mmol) of iodine (12) and 0.333 g (1.46 mmol) of orthoperiodic acid (H5IO6) were added to the mixture in a solid state and were stirred for 2 hours at 80° C. at nitrogen atmosphere so as to form a reaction mixture. After the reaction was completed, the reaction mixture was extracted three times using ethyl ether (50 ml). A collected organic layer was dried using magnesium sulfate and a solvent was evaporated to obtain residue. The obtained residue was separated and purified using silica gel column chromatography, thereby obtaining 3.23 g (yield 87%) of intermediate E as a white solid.

2.73 g (10 mmol) of F-1, 1.1 g (12 mmol) of aniline, 1.44 g (15 mmol) of t-BuONa, 183 mg (0.2 mmol) of Pd2(dba)$_3$, and 40 mg (0.2 mmol) of P(t-Bu)$_3$ were dissolved in 50 ml of toluene so as to form a mixture and then the mixture was stirred for 3 hours at 90° C. so as to form a reaction mixture. After the reaction was completed, the reaction mixture was cooled down to room temperature and then extracted three times using distilled water and 50 ml of diethyl ether. A collected organic layer was dried using magnesium sulfate and a solvent was evaporated to obtain residue. The obtained residue was purified using silica gel column chromatography, thereby obtaining 1.71 g (yield 60%) of intermediate F.

369 mg (1 mmol) of intermediate E, 285 mg (1 mmol) of intermediate F, 300 mg (1.5 mmol) of t-BuONa, 40 mg (0.02 mmol) of Pd2(dba)$_3$, and 3 mg (0.01 mmol) of P(t-Bu)$_3$ were dissolved in 5 ml of toluene so as to form a mixture and then the mixture was stirred for 3 hours at 90° C. so as to form a reaction mixture. After the reaction was completed, the reaction mixture was cooled down to room temperature and then extracted three times using distilled water and 30 ml of diethyl ether. A collected organic layer was dried using magnesium sulfate and a solvent was evaporated to obtain residue. The obtained residue was separated and purified using silica gel column chromatography, thereby obtaining 368 mg (yield 70%) of compound 202.

1H NMR (CDCl3, 300 MHz) δ(ppm) 8.74 (1H), 8.14-7.08 (2H), 7.73-7.41 (8H), 7.38-7.26 (6H), 6.92-6.83 (4H), 6.71-6.61 (3H), 1.74 (6H)

Comparative Example 2

An organic light-emitting device was completely manufactured in the same manner as in Example 1, except that compound 202 was used instead of compound 1 when forming the hole transport layer.

The organic light-emitting device had a current density of 100 mA/cm$^2$, a driving voltage of 6.71 V, color coordinates of (0.143, 0.241), and emission efficiency of 6.52 cd/A.

Comparative Synthesis Example 3

Synthesis of Compound 203

Compound 203 was manufactured through Reaction Formula 5 below:

<Reaction Formula 5>

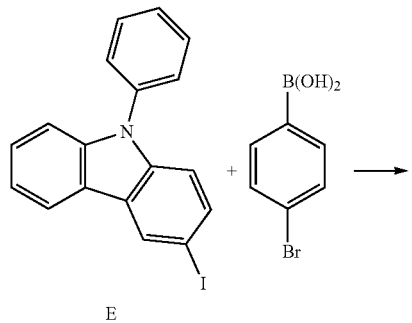
E

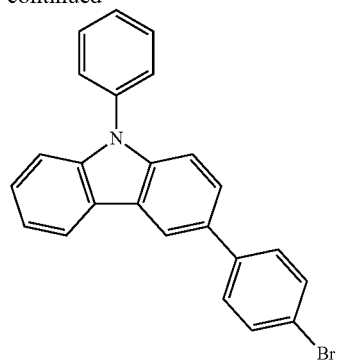
E'

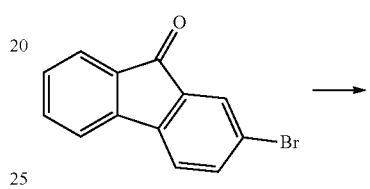

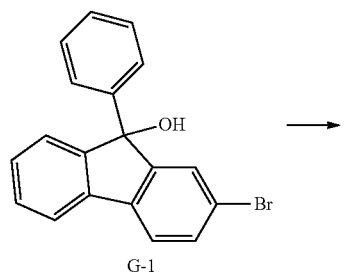
G-1

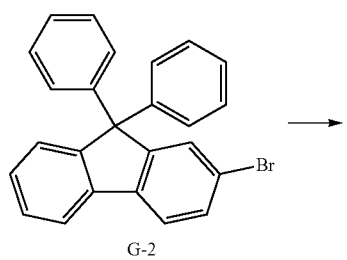
G-2

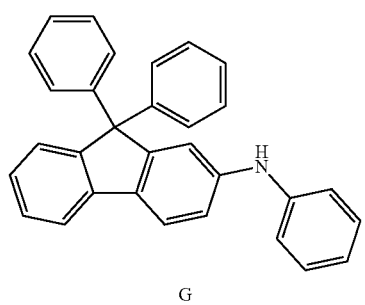
G

E' + G ⟶

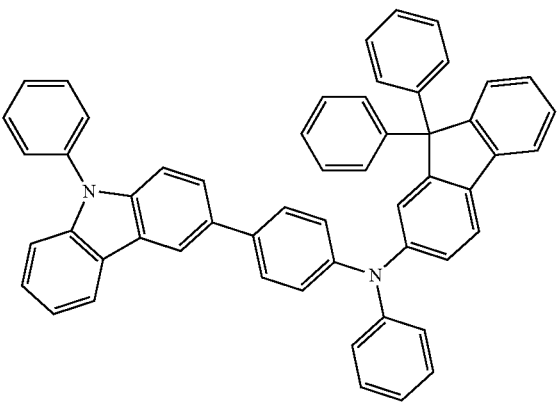

<Compound 203>

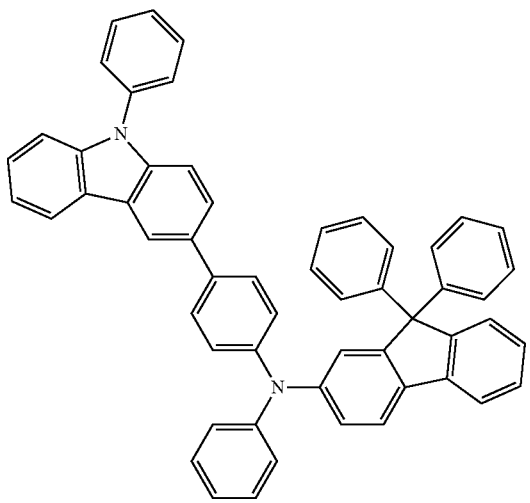

16.6 g (45 mmol) of Compound E, 6 g (30 mmol) of 4-bromophenyl boronic acid, 1.7 g (1.5 mmol) of Pd(PPh3)4, and 20 g (150 mmol) of K₂CO₃ were dissolved in 500 ml of a mixture solution of THF/H2O (2:1) so as to obtain a reaction solution. Then, the reaction solution was extracted three times using 200 ml of diethyl ether. Then, an organic layer was collected and dried using magnesium sulfate and a solvent was evaporated, thereby obtaining residue. The residue was recrystallized to dichloromethane and normal hexane, thereby obtaining 13.4 g (yield 75%) of intermediate E'.

8 g (31.6 mmol) of 2-bromofluorenone was dissolved in 60 ml of THF and then 38 mL (38 mmol) of 1M phenyl magnesium bromide was slowly added at −78° C. so as to form a mixture. After 2 hours, the temperature was maintained at room temperature and the mixture was stirred for 5 hours. The mixture was diluted using 50 ml of an ammonium chloride aqueous solution and then extracted three times using 40 ml of ethyl acetate. A collected organic layer was dried using magnesium sulfate and a solvent was evaporated to obtain residue. The obtained residue was separated and purified using silica gel column chromatography, thereby obtaining 10 g of intermediate G-1 (yield 95%).

10 g (30 mmol) of intermediate G-1 was dissolved in 60 ml of benzene and 2.4 mL (45 mmol) of thick sulphuric acid was added by being diluted in a small amount of benzene so as to form a mixture solution. The mixture solution was stirred for 5 hours at 80° C., benzene was evaporated, and 1N sodium hydroxide aqueous solution was added to the remaining solution to be PH7, and then extracted three times using 40 ml of ethyl acetate. A collected organic layer was dried using magnesium sulfate and a solvent was evaporated to obtain residue. The obtained residue was separated and purified using silica gel column chromatography, thereby obtaining 6 g of intermediate G-2 (yield 50%).

Intermediate G (4.3 g, yield 75%) was obtained in the same manner as above, except that intermediate G-2 was used instead of intermediate B-2 during a synthesis process of compound 2 in Synthesis Example 2. Coupling reaction was subjected to intermediates G and E', thereby synthesizing compound 203 (5.9 g, yield 77%).

1H NMR (CDCl3, 300 MHz) δ(ppm) 8.73 (1H), 8.03-7.92 (3H), 7.81 (1H), 7.73 (2H), 7.68-7.48 (9H), 7.45-7.23 (11H), 7.18-7.05 (4H), 6.85-6.69 (7H)

Comparative Example 3

An organic light-emitting device was completely manufactured in the same mariner as in Example 1, except that compound 203 was used instead of compound 1 when forming the hole transport layer.

The organic light-emitting device had a current density of 100 mA/cm², a driving voltage of 6.83 V, color coordinates of (0.143, 0.241), and emission efficiency of 6.85 cd/A.

Comparative Synthesis Example 4

Synthesis of Compound 204

Compound 204 was manufactured through Reaction Formula 6 below:

<Reaction Formula 6>

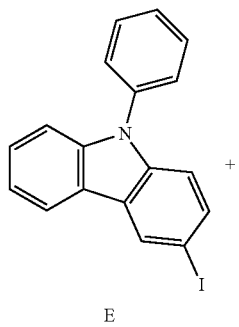

E

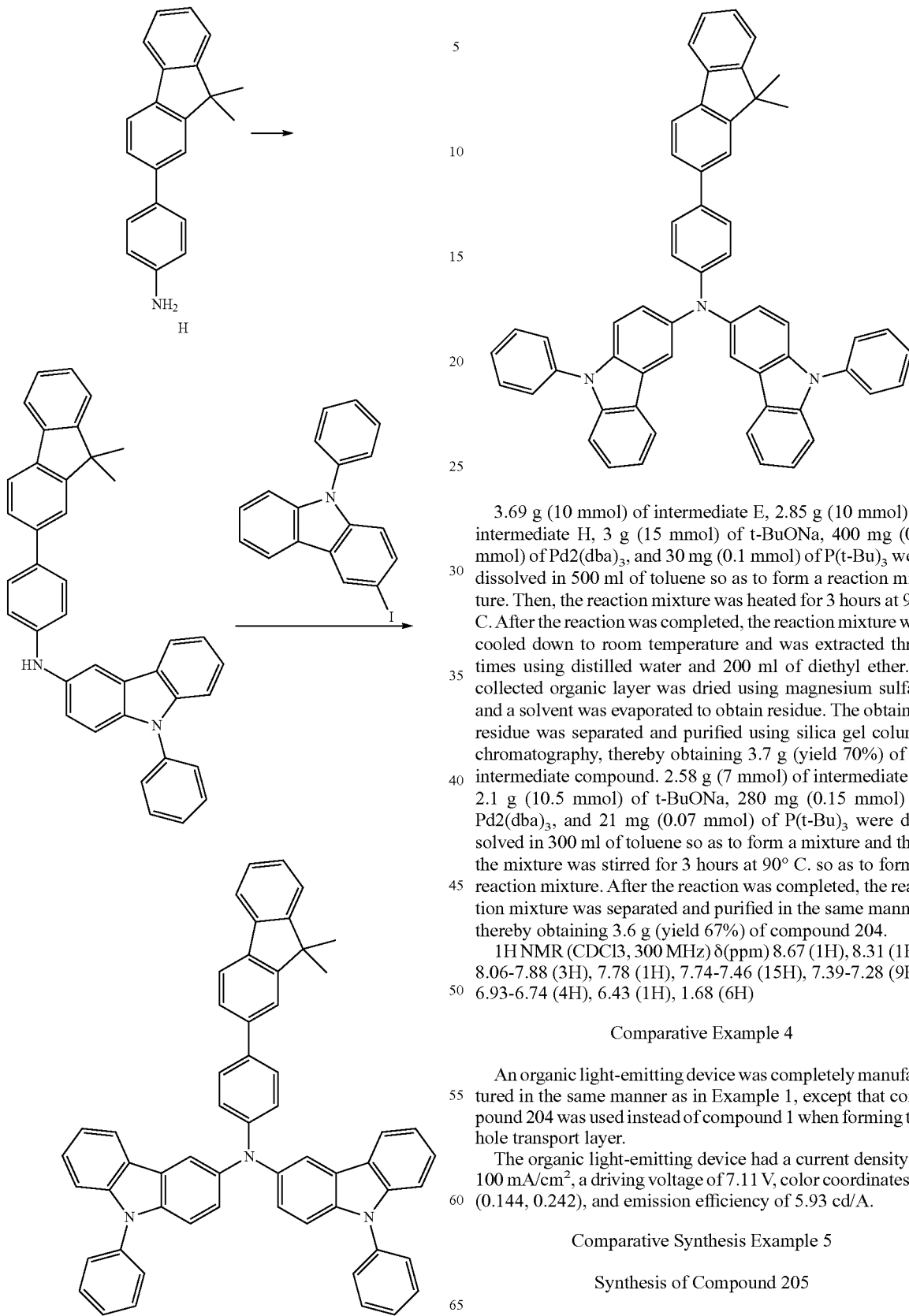

<Compound 204>

3.69 g (10 mmol) of intermediate E, 2.85 g (10 mmol) of intermediate H, 3 g (15 mmol) of t-BuONa, 400 mg (0.2 mmol) of Pd2(dba)₃, and 30 mg (0.1 mmol) of P(t-Bu)₃ were dissolved in 500 ml of toluene so as to form a reaction mixture. Then, the reaction mixture was heated for 3 hours at 90° C. After the reaction was completed, the reaction mixture was cooled down to room temperature and was extracted three times using distilled water and 200 ml of diethyl ether. A collected organic layer was dried using magnesium sulfate and a solvent was evaporated to obtain residue. The obtained residue was separated and purified using silica gel column chromatography, thereby obtaining 3.7 g (yield 70%) of an intermediate compound. 2.58 g (7 mmol) of intermediate E, 2.1 g (10.5 mmol) of t-BuONa, 280 mg (0.15 mmol) of Pd2(dba)₃, and 21 mg (0.07 mmol) of P(t-Bu)₃ were dissolved in 300 ml of toluene so as to form a mixture and then the mixture was stirred for 3 hours at 90° C. so as to form a reaction mixture. After the reaction was completed, the reaction mixture was separated and purified in the same manner, thereby obtaining 3.6 g (yield 67%) of compound 204.

1H NMR (CDCl3, 300 MHz) δ(ppm) 8.67 (1H), 8.31 (1H), 8.06-7.88 (3H), 7.78 (1H), 7.74-7.46 (15H), 7.39-7.28 (9H), 6.93-6.74 (4H), 6.43 (1H), 1.68 (6H)

Comparative Example 4

An organic light-emitting device was completely manufactured in the same manner as in Example 1, except that compound 204 was used instead of compound 1 when forming the hole transport layer.

The organic light-emitting device had a current density of 100 mA/cm², a driving voltage of 7.11 V, color coordinates of (0.144, 0.242), and emission efficiency of 5.93 cd/A.

Comparative Synthesis Example 5

Synthesis of Compound 205

Compound 205 was manufactured through Reaction Formula 7 below:

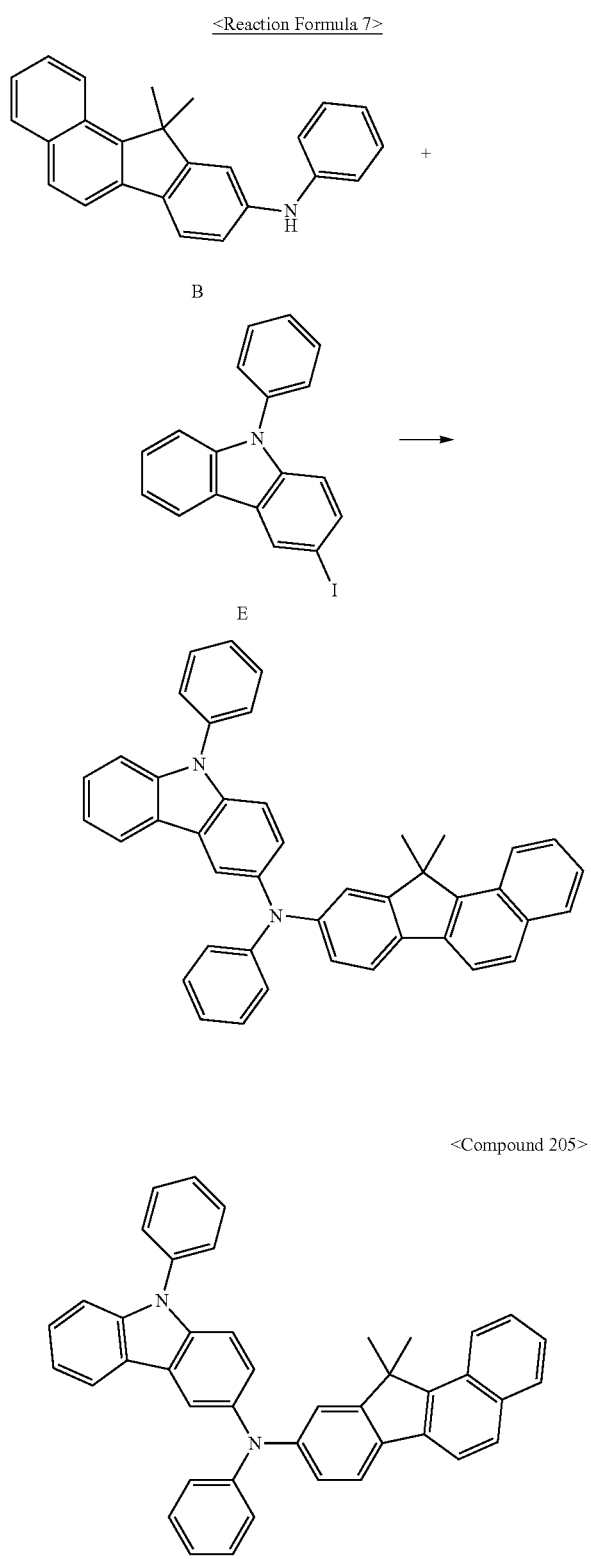

<Reaction Formula 7>

B

E

<Compound 205>

Compound 205 was synthesized in the same manner using intermediates B and E.

1H NMR (CDCl3, 300 MHz) δ(ppm) 8.72 (1H), 8.28 (1H), 8.07-7.95 (3H), 7.85 (2H), 7.63-7.47 (7H), 7.41-7.29 (5H), 7.028-6.85 (4H), 6.73 (3H), 1.79 (6H)

Comparative Example 5

An organic light-emitting device was completely manufactured in the same manner as in Example 1, except that compound 205 was used instead of compound 1 when forming the hole transport layer.

The organic light-emitting device had a current density of 100 mA/cm$^2$, a driving voltage of 6.85 V, color coordinates of (0.143, 0.242), and emission efficiency of 6.64 cd/A.

Evaluation Example

The organic light-emitting devices of Examples 1 through 5 and the organic light-emitting devices of Comparative Examples 1 through 5 were evaluated in terms of current density, driving voltage, efficiency, and half-luminance lifetime using PR650 (Spectroscan) Source Measurement Unit (PhotoResearch Co. LTD.). The results are shown in Table 1 below (half-luminance lifetime was measured at an applied current of 4 mA)

TABLE 1

| | Electron transport layer | Driving voltage (V) | Current density (mA/cm$^2$) | Emission Efficiency (cd/A) | Half-luminance lifetime (h) |
|---|---|---|---|---|---|
| Example 1 | Compound 1 | 6.63 | 100 | 7.11 | 362 |
| Example 2 | Compound 2 | 6.75 | 100 | 7.34 | 370 |
| Example 3 | Compound 3 | 6.59 | 100 | 7.21 | 334 |
| Example 4 | Compound 4 | 6.69 | 100 | 7.09 | 358 |
| Example 5 | Compound 5 | 6.78 | 100 | 7.28 | 348 |
| Comparative Example 1 | NPB | 7.82 | 100 | 5.72 | 273 |
| Comparative Example 2 | Compound 202 | 6.71 | 100 | 6.52 | 226 |
| Comparative Example 3 | Compound 203 | 6.83 | 100 | 6.85 | 258 |
| Comparative Example 4 | Compound 204 | 7.11 | 100 | 5.93 | 183 |
| Comparative Example 5 | Compound 205 | 6.85 | 100 | 6.64 | 251 |

According to Table 1, emission efficiencies and half-luminance lifetimes of the organic light-emitting devices of Examples 1 through 5 are higher and longer than those of the organic light-emitting devices of Comparative Examples 1 through 5. Also, the driving voltages of the organic light-emitting devices of Examples 1, 3, and 4 are lower than those of the organic light-emitting devices of Comparative Examples 1 through 5. In this regard, the organic light-emitting devices of Examples 1 through 5 have excellent performance, for example, high emission efficiencies and long lifetime.

The organic light-emitting device including the condensed-cyclic compound represented by Formula 1 has high emission efficiency and long lifetime and thus a flat panel display apparatus has excellent performance.

While the present invention has been particularly shown and described with is reference to exemplary embodiments thereof, it will be understood by those of ordinary skill in the art that various changes in form and details may be made therein without departing from the spirit and scope of the present invention as defined by the following claims.

What is claimed is:

1. A condensed-cyclic compound represented by Formula 1 below:

<Formula 1>

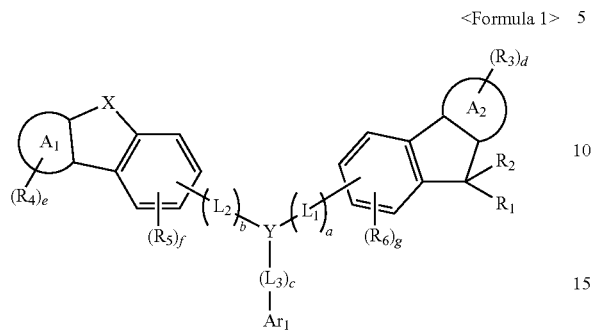

wherein X is N(Ar$_2$) or S;

Y is N, B, or P;

A$_1$ and A$_2$ are bicyclic aromatic rings;

L$_1$, L$_2$ and L$_3$ are each independently one selected from the group consisting of a substituted or unsubstituted C$_1$-C$_{30}$ alkylene group, a substituted or unsubstituted C$_5$-C$_{30}$ arylene group, and a substituted or unsubstituted divalent C$_2$-C$_{30}$ heterocyclic group;

Ar$_1$ and Ar$_2$ are each independently one selected from the group consisting of a hydrogen atom, deuterium, a halogen atom, a hydroxyl group, a cyano group, a nitro group, a carboxyl group, a substituted or unsubstituted C$_1$-C$_{30}$ alkyl group, a substituted or unsubstituted C$_2$-C$_{30}$ alkenyl group, a substituted or unsubstituted C$_2$-C$_{30}$ alkynyl group, a substituted or unsubstituted C$_1$-C$_{30}$ alkoxy group, a substituted or unsubstituted C$_3$-C$_{30}$ is cycloalkyl group, a substituted or unsubstituted C$_3$-C$_{30}$ cycloalkenyl group, a substituted or unsubstituted C$_5$-C$_{30}$ aryl group, a substituted or unsubstituted C$_5$-C$_{30}$ aryloxy group, a substituted or unsubstituted C$_5$-C$_{30}$ arylthio group, a substituted or unsubstituted C$_2$-C$_{30}$ heterocyclic group, a group represented by N(Q$_1$)(Q$_2$), and a group represented by Si(Q$_3$)(Q$_4$)(Q$_5$), Q$_1$ through Q$_5$ are each independently one selected from the group consisting of a hydrogen atom, deuterium, a halogen atom, a hydroxyl group, a cyano group, an amino group, a nitro group, a carboxyl group, a substituted or unsubstituted C$_1$-C$_{30}$ alkyl group, a substituted or unsubstituted C$_2$-C$_{30}$ alkenyl group, a substituted or unsubstituted alkynyl group, a substituted or unsubstituted C$_1$-C$_{30}$ alkoxy group, a substituted or unsubstituted C$_3$-C$_{30}$ cycloalkyl group, a substituted or unsubstituted C$_3$-C$_{30}$ cycloalkenyl group, a substituted or unsubstituted C$_5$-C$_{30}$ aryl group, a substituted or unsubstituted C$_5$-C$_{30}$ aryloxy group, a substituted or unsubstituted C$_5$-C$_{30}$ arylthio group, and a substituted or unsubstituted C$_2$-C$_{30}$ heterocyclic group;

R$_1$, R$_2$, R$_3$, R$_4$, R$_5$, and R$_6$ are each independently one selected from the group consisting of a hydrogen atom, deuterium, a halogen atom, a hydroxyl group, a cyano group, an amino group, a nitro group, a carboxyl group, a substituted or unsubstituted C$_1$-C$_{30}$ alkyl group, a substituted or unsubstituted C$_2$-C$_{30}$ alkenyl group, a substituted or unsubstituted C$_2$-C$_{30}$ alkynyl group, a substituted or unsubstituted C$_1$-C$_{30}$ alkoxy group, a substituted or unsubstituted C$_3$-C$_{30}$ cycloalkyl group, a substituted or unsubstituted C$_3$-C$_{30}$ cycloalkenyl group, a substituted or unsubstituted C$_5$-C$_{30}$ aryl group, a substituted or unsubstituted C$_5$-C$_{30}$ aryloxy group, a substituted or unsubstituted C$_5$-C$_{30}$ arylthio group, and a substituted or unsubstituted C$_2$-C$_{30}$ heterocyclic group, wherein at least two of R$_3$ through R$_6$ that are adjacent to each other may be combined with each other to form a saturated or unsaturated ring and plural groups in R$_3$ through R$_6$ may be the same as each other or different from each other; and a, b, and c are each independently numbers from 0 to 5, d and e are each independently numbers from 1 to 10, and f and g are each independently numbers from 1 to 3.

2. The condensed-cyclic compound of claim 1, wherein X is N(Ar$_2$) and Ar$_2$ is as defined in claim 1.

3. The condensed-cyclic compound of claim 1, wherein Y is N.

4. The condensed-cyclic compound of claim 1, wherein A$_1$ and A$_2$ are C$_8$-C$_{10}$ bicyclic aromatic rings.

5. The condensed-cyclic compound of claim 1, wherein A$_1$ and A$_2$ are each independently a naphthalene ring or an indene ring.

6. The condensed-cyclic compound of claim 1, wherein

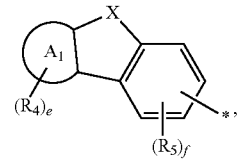

in Formula 1, is represented by one of Formulas 2A through 2C below:

<Formula 2A>

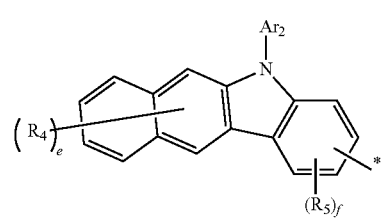

<Formula 2B>

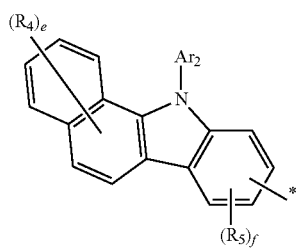

<Formula 2C>

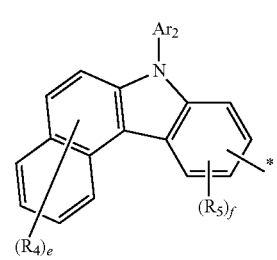

wherein Ar$_2$ is one selected from the group consisting of a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group, and e is a number from 1 to 6, and * represents a chemical bond.

7. The condensed-cyclic compound of claim 1, wherein

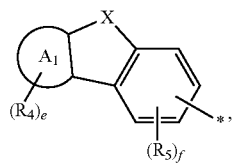

in Formula 1, is represented by one of Formulas 3A through 3C below:

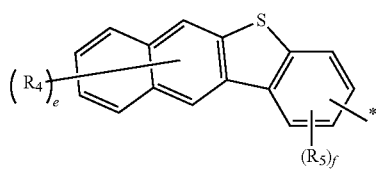
<Formula 3A>

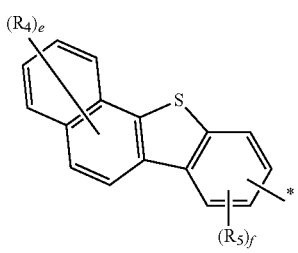
<Formula 3B>

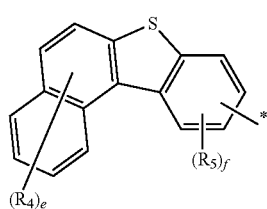
<Formula 3C> wherein e is one of fixed numbers from 1 to 6, and * represents a chemical bond.

8. The condensed-cyclic compound of claim 1, wherein

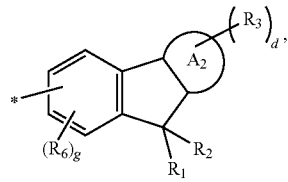

in Formula 1, is represented by one of Formulas 4A through 4C below:

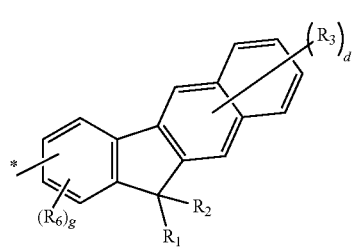
<Formula 4A>

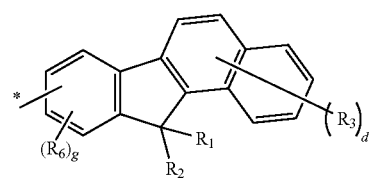
<Formula 4B>

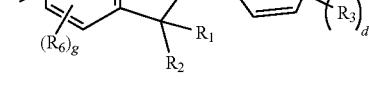

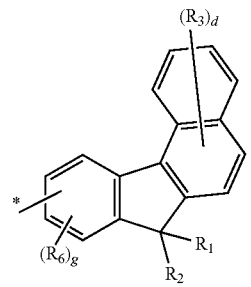
<Formula 4C> wherein, R$_1$ and R$_2$ are each independently one selected from the group consisting of a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group, and d is a number from 1 to 6 and * represents a chemical bond.

9. The condensed-cyclic compound of claim 1, wherein the condensed-cyclic compound represented by Formula 1 above is represented by one of Formulas 5A through 5I below:

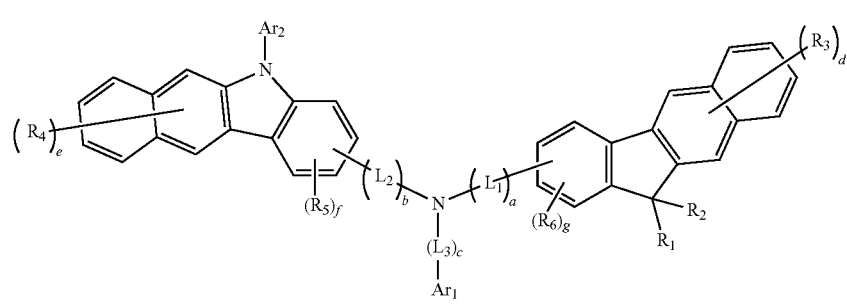
<Formula 5A>
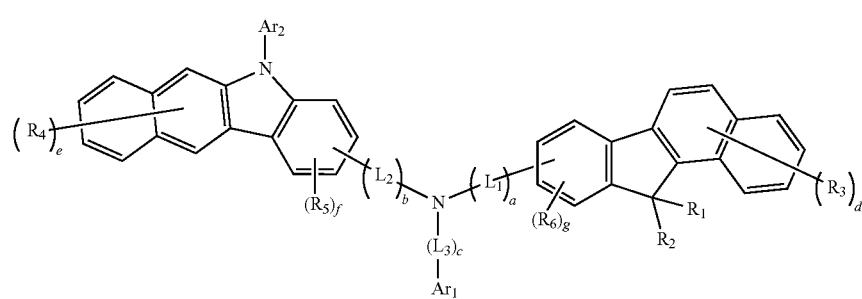
<Formula 5B>
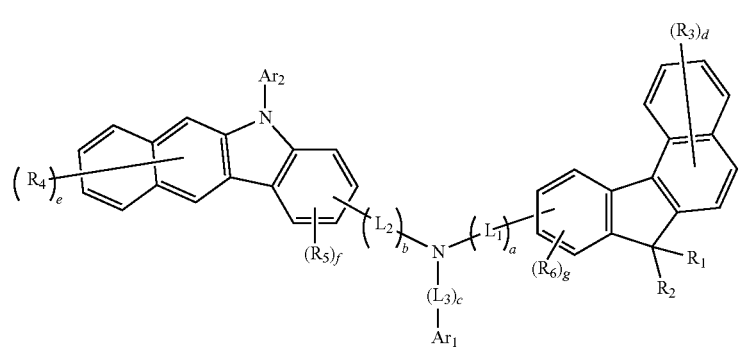
<Formula 5C>
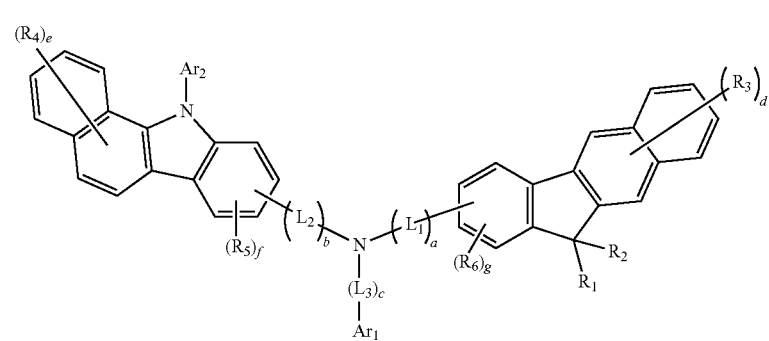
<Formula 5D>
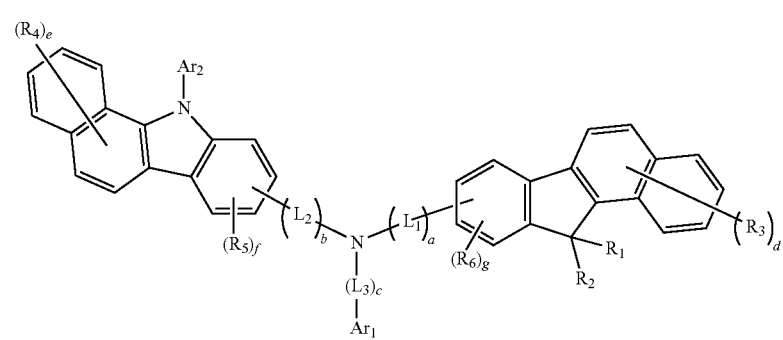
<Formula 5E>

<Formula 5F>

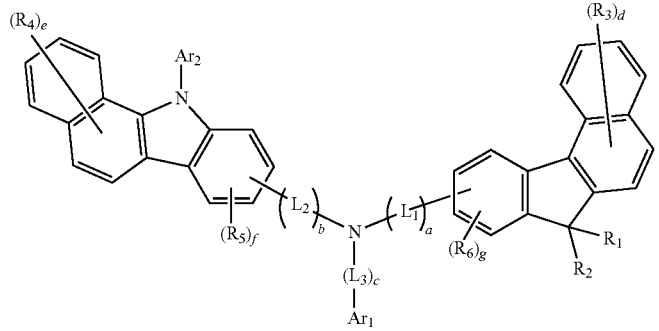

<Formula 5G>

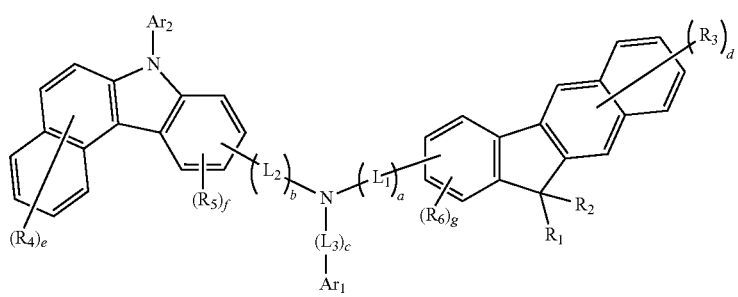

<Formula 5H>

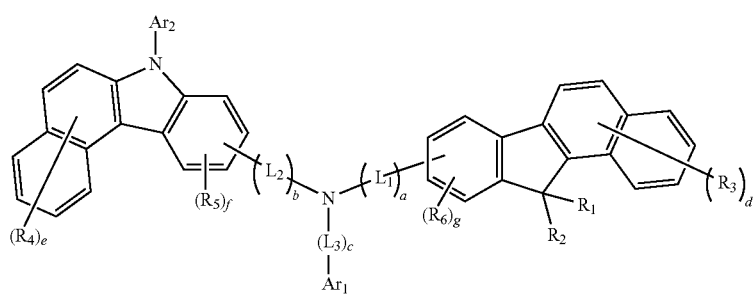

<Formula 5I>

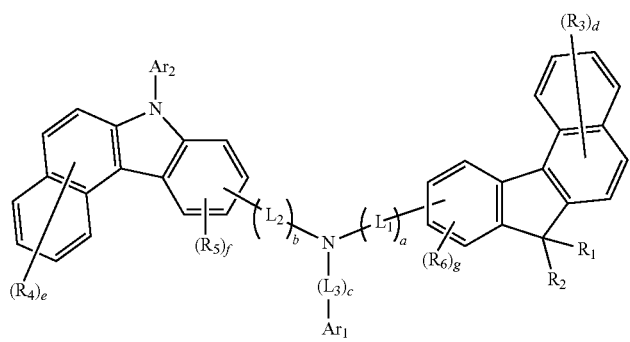

wherein, $Ar_1$ and $Ar_2$ are each independently one selected from the group consisting of a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group;

$R_1$ and $R_2$ are each independently one selected from the group consisting of a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group; and d and e are each independently numbers from 1 to 6.

10. The condensed-cyclic compound of claim 1, wherein $L_1$, $L_2$, and $L_3$ are each independently one selected from the group consisting of a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, and a substituted or unsubstituted hexacenylene group.

11. The condensed-cyclic compound of claim 1, wherein a, b, and c are each independently 0 or 1.

12. The condensed-cyclic compound of claim 1, wherein $A_1$ and $Ar_2$ are each independently one selected from the group consisting of a hydrogen atom, deuterium, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphtyl group, a substituted to or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoxazolyl group, a substituted or unsubstituted benzoimidazolyl group, a substituted or unsubstituted furanyl, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzoxazolyl group, a substituted or unsubstituted dibenzofuranyl group, a substituted or unsubstituted dibenzothiophenyl group, a group represented by $N(Q_1)(Q_2)$, and a group represented by $Si(Q_3)(Q_4)(Q_5)$ where $Q_1$ through $Q_5$ are as defined in claim 1.

13. The condensed-cyclic compound of claim 1, $R_1$ and $R_2$ are each independently one selected from the group consisting of a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, and a substituted or unsubstituted pyridazinyl group, and $R_3$, $R_4$, $R_5$, and $R_6$ are hydrogen atoms.

14. The condensed-cyclic compound of claim 1, wherein the condensed-cyclic compound represented by Formula 1 is one of compounds represented by Compounds 1 through 15 below:

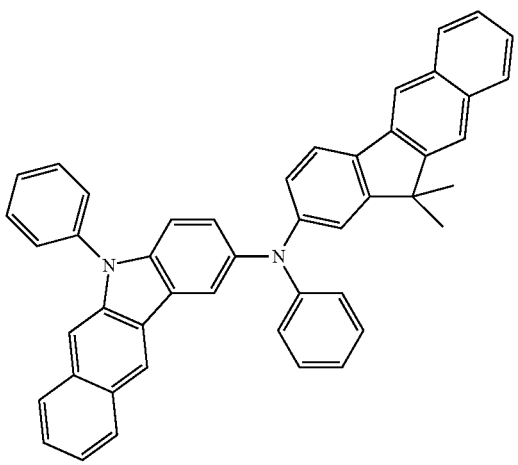

<Compound 1>

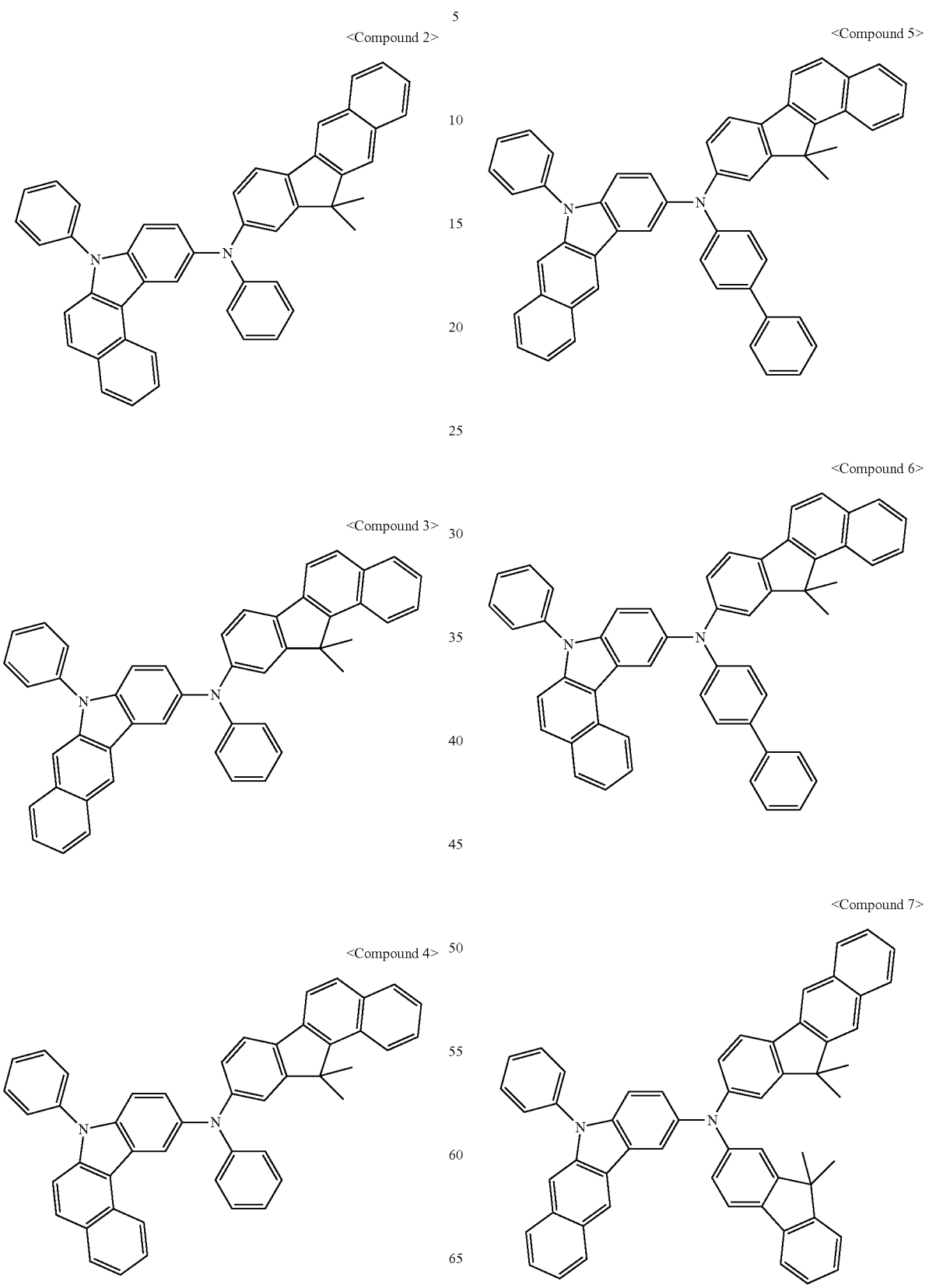

<Compound 8>
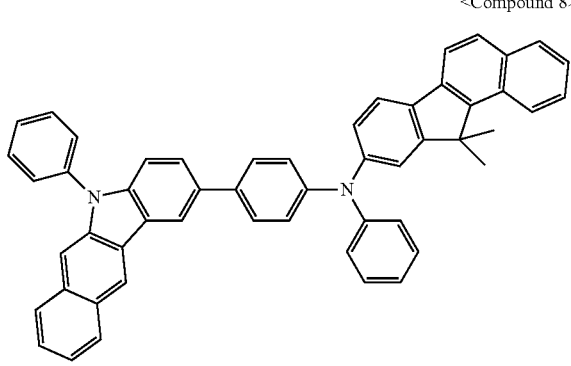
<Compound 9>
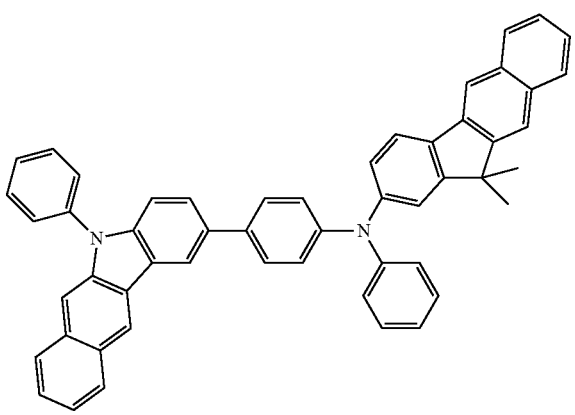
<Compound 10>
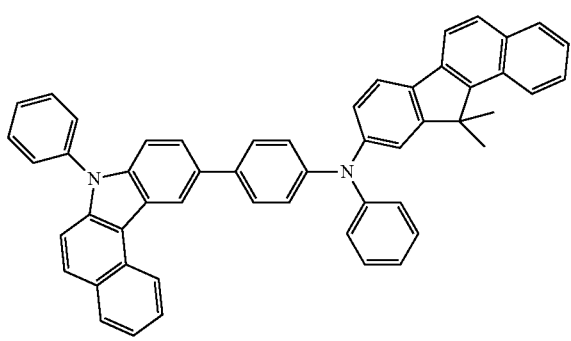
<Compound 11>
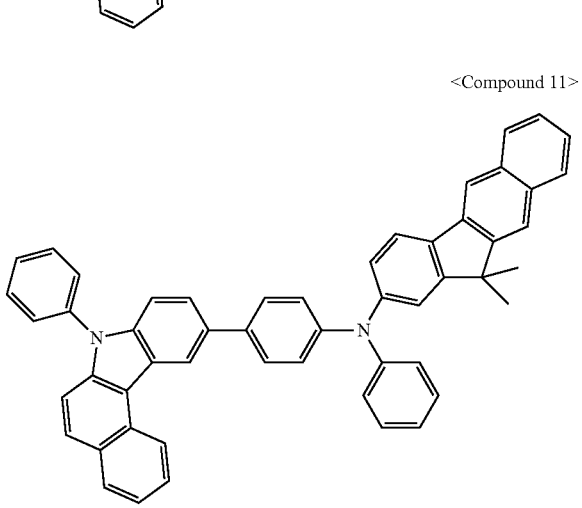
<Compound 12>
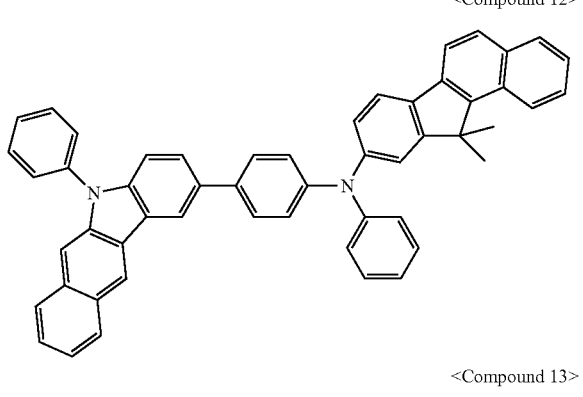
<Compound 13>
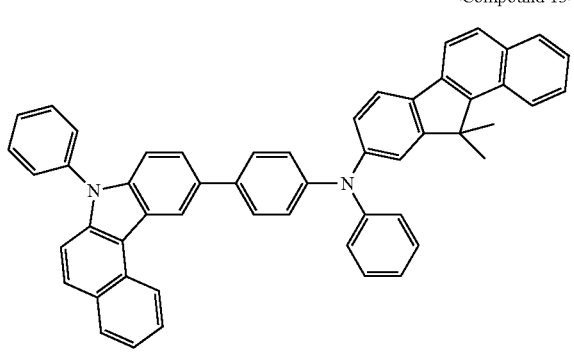
<Compound 14>
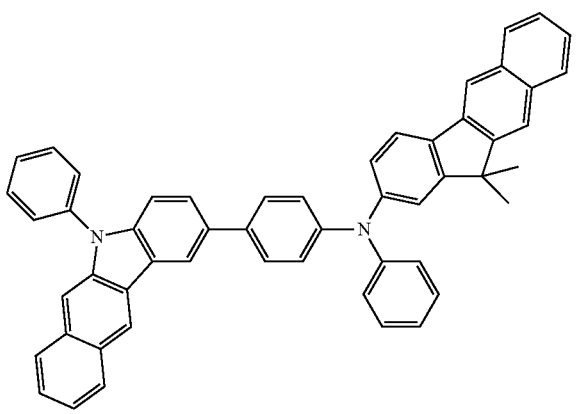
<Compound 15>
15. An organic light-emitting device comprising:
a first electrode;
a second electrode; and an organic light-emitting device comprising at least one organic layer interposed between the first electrode and the second electrode, wherein the at least one organic layer comprises a condensed-cyclic compound of claim 1.

16. The organic light-emitting device of claim 15, wherein the organic layer comprises a hole injection layer, a hole transport layer, or a single layer simultaneously having a hole injection function and a hole transport function.

17. The organic light-emitting device of claim 15, further comprising at least one emission layer interposed between the first electrode and the second electrode, wherein the at least one organic layer is the hole transport layer and the emission layer comprises a fluorescent or phosphorescent host.

18. The organic light-emitting device of claim 15, wherein the at least one organic layer is an emission layer.

19. The organic light-emitting device of claim 15, further comprising between the first electrode and the second electrode at least one selected from the group consisting of a hole injection layer, a hole transport layer, an electron blocking layer, a hole blocking layer, an electron transport layer, and an electron injection layer.

20. A flat panel display apparatus comprising a transistor comprising a source electrode, a drain electrode, a gate, and an active layer, and the organic light-emitting device of claim 15, wherein a first electrode of the organic light-emitting device is electrically connected to the source electrode or the drain electrode.

* * * * *